(12) United States Patent
Ouyang et al.

(10) Patent No.: US 9,795,951 B2
(45) Date of Patent: Oct. 24, 2017

(54) DELAMINATION OF BOROSILICATE LAYERED ZEOLITE

(71) Applicants: Xiaoying Ouyang, El Cerrito, CA (US); Alexander Katz, Richmond, CA (US); Stacey Ian Zones, San Francisco, CA (US)

(72) Inventors: Xiaoying Ouyang, El Cerrito, CA (US); Alexander Katz, Richmond, CA (US); Stacey Ian Zones, San Francisco, CA (US)

(73) Assignees: Chevron U.S.A. Inc., San Ramon, CA (US); The Regents of the University of California, Oakland, CA (US)

( * ) Notice: Subject to any disclaimer, the term of this patent is extended or adjusted under 35 U.S.C. 154(b) by 420 days.

(21) Appl. No.: 14/291,489

(22) Filed: May 30, 2014

(65) Prior Publication Data

US 2014/0356280 A1 Dec. 4, 2014

Related U.S. Application Data

(60) Provisional application No. 61/829,986, filed on May 31, 2013, provisional application No. 61/901,184, filed on Nov. 7, 2013.

(51) Int. Cl.
| | |
|---|---|
| *B01J 29/86* | (2006.01) |
| *C02F 1/42* | (2006.01) |
| *C07D 307/48* | (2006.01) |
| *C07H 1/00* | (2006.01) |
| *C07H 3/02* | (2006.01) |
| *C07D 301/03* | (2006.01) |

(Continued)

(52) U.S. Cl.
CPC ............ *B01J 29/86* (2013.01); *B01J 20/186* (2013.01); *B01J 29/048* (2013.01); *B01J 29/70* (2013.01); *B01J 29/7038* (2013.01); *B01J 29/87* (2013.01); *B01J 29/89* (2013.01); *B01J 35/002* (2013.01); *B01J 39/14* (2013.01); *C07D 301/03* (2013.01); *C07D 307/48* (2013.01); *B01J 2229/16* (2013.01); *B01J 2229/183* (2013.01); *B01J 2229/37* (2013.01); *C02F 1/281* (2013.01); *C02F 1/42* (2013.01)

(58) Field of Classification Search
CPC ...................................................... B01J 29/86
See application file for complete search history.

(56) References Cited

U.S. PATENT DOCUMENTS

| | | |
|---|---|---|
| 5,061,466 A | 10/1991 | Chang et al. |
| 7,084,087 B2 | 8/2006 | Shan et al. |

(Continued)

OTHER PUBLICATIONS

Delaminated zeolite precursors as selective acidic catalysts A. Corma et al. Nature, vol. 396, pp. 353-356, 1998.*

(Continued)

*Primary Examiner* — Douglas B Call
(74) *Attorney, Agent, or Firm* — E. Joseph Gess; Melissa M. Hayworth

(57) ABSTRACT

Provided is a surfactant-free, single-step synthesis of delaminated aluminosilicate zeolites. The process comprises the step of heating a borosilicate zeolite precursor in a metal salt solution, e.g., an aluminum nitrate solution, zinc nitrate solution or manganese nitrate solution. The delaminated aluminosilicate zeolite product is then recovered from the solution.

20 Claims, 23 Drawing Sheets

(51) Int. Cl.
  *B01J 29/70* (2006.01)
  *B01J 29/87* (2006.01)
  *B01J 35/00* (2006.01)
  *B01J 39/14* (2006.01)
  *B01J 20/18* (2006.01)
  *B01J 29/04* (2006.01)
  *B01J 29/89* (2006.01)
  *C02F 1/28* (2006.01)

(56) References Cited

U.S. PATENT DOCUMENTS

2002/0164283 A1* 11/2002 Jones .................. C01B 37/00
                                                       423/702
2003/0004382 A1*  1/2003 Van Den Brink ....... B01J 29/04
                                                       585/467
2003/0133870 A1   7/2003 Chen et al.

OTHER PUBLICATIONS

Layered Materials with Catalytic Applications: Pillared and Delaminated Zeolites from MWW Precursors Urbano Diaz International Scholarly Research Network: Chemical Engineering Volumn 2012, article ID 537164, pp. 1-35, Aug. 2012.*

L. Liu et al., "Synthesis, characterization, and catalytic properties of MWW zeolite with variable Si/Al ratios", Microporous and Mesoporous Materials, 2006, vol. 94. pp. 304-312.

I. Ogino et al., "Heteroatom-Tolerant Delamination of Layered Zeolite Precursor Materials", Chemistry of Materials, Feb. 2013, vol. 25, pp. 1502-1509.

International Search Report from corresponding PCT Application No. PCT/US2014/040214 mailed on Sep. 26, 2014.

* cited by examiner

DELAMINATION OF BOROSILICATE LAYERED ZEOLITE

RELATED APPLICATIONS

This application claims priority to U.S. Provisional Patent Application Ser. No. 61/829,986 filed 31 May 2013 and U.S. Provisional Patent Application Ser. No. 61/901,184 filed 7 Nov. 2013, the contents of both of which are hereby incorporated by reference in their entireties.

BACKGROUND OF THE INVENTION

Field of the Invention

The present invention relates to novel delaminated metallosilicate zeolite materials and methods of preparing such materials. More specifically, provided is a simple, surfactant-free, one-step synthesis for delaminating borosilicate layered zeolite precursors.

Description of the Related Art

Zeolites demonstrate extraordinary catalytic utility due to their well-defined catalytic active sites consisting of heteroatoms substituted within the zeolitic framework as well as shape selectivities. However, zeolites have been limited to microporous frameworks in the past, which has limited reactant substrates to small molecules. Incorporating greater accessibility into zeolite catalysts would be invaluable to expanding the scope of their catalysis to include larger and sterically more bulky substrate and product molecules, and has served as a lofty goal in the synthesis of this class of materials. Over the years, there have been many elegant enabling efforts towards this goal, including synthesis of extra-large pore zeolites, (see Davis, M. E. *Chemistry-a European Journal* 1997, 3, 1745 and Jiang, J.; Yu, J.; Corma, A. *Angewandte Chemie-International Edition* 2010, 49, 3120), delaminated layered zeolite precursor materials, (Corma, A.; Fornes, V.; Pergher, S. B.; Maesen, T. L. M.; Buglass, J. G. *Nature* 1998, 396, 353; Ogino, I.; Nigra, M. M.; Hwang, S.-J.; Ha, J.-M.; Rea, T.; Zones, S. I.; Katz, A. *Journal of the American Chemical Society* 2011, 133, 3288; Eilertsen, E. A.; Ogino, I.; Hwang, S.-J.; Rea, T.; Yeh, S.; Zones, S. I.; Katz, A. *Chemistry of Materials* 2011, 23, 5404; Ogino, I.; Eilertsen, E. A.; Hwang, S.-J.; Rea, T.; Xie, D.; Ouyang, X.; Zones, S. I.; Katz, A. *Chemistry of Materials* 2013; and Maheshwari, S.; Jordan, E.; Kumar, S.; Bates, F. S.; Penn, R. L.; Shantz, D. F.; Tsapatsis, M. *Journal of the American Chemical Society* 2008, 130, 1507), single-unit-cell zeolite nanosheets (see Choi, M.; Na, K.; Kim, J.; Sakamoto, Y.; Terasaki, O.; Ryoo, R. *Nature* 2009, 461, 246), hierachically nanoporous zeolitelike materials (Na, K.; Jo, C.; Kim, J.; Cho, K.; Jung, J.; Seo, Y.; Messinger, R. J.; Chmelka, B. F.; Ryoo, R. *Science* 2011, 333, 328) and self-pillared zeolite nanosheets (Zhang, X.; Liu, D.; Xu, D.; Asahina, S.; Cychosz, K. A.; Agrawal, K. V.; Al Wahedi, Y.; Bhan, A.; Al Hashimi, S.; Terasaki, O.; Thommes, M.; Tsapatsis, M. *Science* 2012, 336, 1684). Nevertheless, all of these approaches, while beautiful in their own right and highly successful for providing larger molecules with catalytic accessibility to zeolites, require an intricate self-assembly between organic surfactants and the inorganic zeolite framework. These surfactants are costly to synthesize and render the process of accessible zeolite synthesis less atom efficient, since they are typically irreversibly consumed (e.g. calcination) prior to use. An emerging approach for synthesis of accessible zeolitic structures that does not require organic surfactants includes synthesis of MCM-56 analogues, which consist of disordered sheets of zeolite layers, using mild acid treatment of the as-made MWW layered zeolite precursors, which removes some of the structure-directing agent. Such materials, when substituted with metal heteroatoms, have shown catalytic activity using sterically bulky reactants, such as Ti-catalyzed epoxidation of cyclooctene using tertbutylhydroperoxide as oxidant; Al-catalyzed cracking of 1,3,5-triisopropylbenzene, and Sncatalyzed Baeyer-Villiger oxidation of 2-adamantanone (Wang, L.; Wang, Y.; Liu, Y.; Chen, L.; Cheng, S.; Gao, G.; He, M.; Wu, P. *Microporous and Mesoporous Materials* 2008, 113, 435; Wang, Y.; Liu, Y.; Wang, L.; Wu, H.; Li, X.; He, M.; Wu, P. *Journal of Physical Chemistry C* 2009, 113, 18753; and Liu, G.; Jiang, J.-G.; Yang, B.; Fang, X.; Xu, H.; Peng, H.; Xu, L.; Liu, Y.; Wu, P. *Microporous and Mesoporous Materials* 2013, 165, 210.) Another promising approach for synthesis of accessible zeolites is the transformation of three-dimensional UTL germanosilicate into a two-dimensional lamellar zeolite by Cejka et al., who demonstrated that layers are separated during hydrolysis of the double-four ring (D4R) bridging units by hydrolysis (Roth, W. J.; Shvets, O. V.; Shamzhy, M.; Chlubna, P.; Kubu, M.; Nachtigall, P.; Cejka, J. *Journal of the American Chemical Society* 2011, 133, 6130; and Chlubna, P.; Roth, W. J.; Greer, H. F.; Zhou, W.; Shvets, O.; Zukal, A.; Cejka, J.; Morris, R. E. *Chemistry of Materials* 2013, 25, 542.) This latter approach, while elegant, requires precursors to consist of D4R units in the space between layers, such that D4R removal via hydrolysis results in two-dimensional zeolite layers, and has only been synthetically demonstrated on zeolite UTL.

Borosilicate zeolites have historically been generally considered to be less useful for acid-catalyzed reactions because their intrinsically weak acidity can effectively catalyze reactions that require mild acidity (Millini, R.; Perego, G.; Bellussi, G. *Topics in Catalysis* 1999, 9, 13; Chen, C. Y., Zones, S. I., Hwang, S. J., Bull, L. M. In *Recent Advances in the Science and Technology of Zeolites and Related Materials, Pts a-C*; VanSteen, E., Claeys, M., Callanan, L. H., Eds. 2004; Vol. 154, p 1547; and Chen, C. Y., Zones, S. I. In 13*th International Zeolite Conference*; Galarneau, A., Di Renzo, F., Fujula, F., Vedrine, J., Eds.; Elsevier: Amsterdam, 2001, p paper 26.) However, borosilicate zeolites provide a unique route for synthesizing many types of isomorphous forms of zeolites at certain Si/M ratios (M=Al, Ga, Ti, etc.), which offer opportunities for synthesizing heteroatom-substituted metallosilicate zeolites, where the metal ions might otherwise be difficult to incorporate into the framework during direct synthesis (Chen, C. Y.; Zones, S. I. In 13*th International Zeolite Conference*; Galarneau, A., Di Renzo, F., Fujula, F., Vedrine, J., Eds.; Elsevier: Amsterdam, 2001, p paper 11.) In such a modification of one framework metal for another, the B atoms templates certain T-positions in the zeolitic framework, and silanol nests can be created upon deboronation (Deruiter, R.; Kentgens, A. P. M.; Grootendorst, J.; Jansen, J. C.; Vanbekkum, H. *Zeolites* 1993, 13, 128; and Hwang, S. J.; Chen, C. Y.; Zones, S. I. *Journal of Physical Chemistry B* 2004, 108, 18535.) Such silanol nests can be re-occupied via tetrahedral molecular recognition by another metal ion, which has a size and oxygen coordination geometry similar to B in the framework, which favors formation of tetrahedral $MO_4$ sites. It has been discovered that treatment of borosilicate zeolites with $Al(NO_3)_3$ solution in a single step successfully exchanges B sites in 12-membered rings (12MR) or on the external surface with Al sites. The resulting sites exhibit strong Brønsted acidity. However, it has also been demonstrated heretofore that it is not possible to exchange B sites that are located in 10 MR, presumably due to the bulkiness of $Al(H_2O)_6^{3+}$ hydrated cations.

Zeolite catalysts, in general, consisting of microporous crystalline aluminosilicates, are widely used in petroleum refining and fine-chemical synthesis because their strong acid sites within uniform micropores give both high activities and shape selectivities. However, their applications are limited to small-molecule synthesis due to small aperture size (<2 nm) of micropores. Delaminated zeolites are very desirable due to their high accessibility for bulky molecules, but typically require expensive organic surfactants to affect delamination. Other large-molecule accessible zeolites include extra-large pore zeolites, single-unit-cell zeolite nanosheets, hierachically nanoporous zeolitelike materials, and self-pillared zeolite nanosheets, but all require surfactants for synthesis.

Of value to the industry would be a suitable synthesis which is simple and more economical, e.g., not requiring the use of a surfactant.

SUMMARY OF THE INVENTION

Provided is a surfactant-free, single-step synthesis of delaminated metallosilicate zeolites. The process comprises the step of heating a borosilicate zeolite precursor in a metal salt solution. If the said borosilicate zeolite precursor is heated in an aluminum nitrate solution, the resulting material is a delaminated aluminosilicate zeolite with high density of tetrahedral aluminum sites located in 12-MR pockets on the external surface. On the other hand, if the said borosilicate zeolite precursor is heated in a salt solution of either zinc nitrate solution or manganese nitrate solution, the resulting material is a delaminated zeolite consisting of a high density of vacant silanol nests, which are located within 12-MR pockets on the external surface. The delaminated aluminosilicate, or the delaminated silanol-nest-containing zeolite product, is then recovered from the solution. Such results pertaining to synthesis of delaminated materials and specific compositions mentioned above under these mild conditions of salt treatment are unprecedented and unexpected.

The procedure for synthesizing delaminated aluminosilicate zeolites is simple and is demonstrated, for example, by heating a borosilicate zeolite precursor, ERB-1P, in aluminum nitrate solution. The synthesis can be done in a single step with nearly 100% silica yield, which is much more convenient and economical than conventional delamination involving the use of organic surfactants and sonication. The resulting materials prepared in this new delamination method possess disordered stacking of thin zeolitic sheets (~2.5 nm) along the c-axis, and a high density of strong acid sites on the external surface. This structure facilitates many acid-catalyzed reactions, especially those containing bulky molecules. The present novel synthesis can be applied to large-scale production of delaminated aluminosilicate zeolites, and potentially expand the applications of zeolites in petrochemical, fine chemical and pharmaceutical industries where bulky substrates are often used.

The procedure of synthesizing delaminated silanol-nest-containing zeolites is simple and is demonstrated, for example, by heating a borosilicate zeolite precursor, ERB-1P, in zinc nitrate solution at pH of ~1. The synthesis can be performed in a single step with nearly 100% silica yield. Both the synthesis method and the resulting delaminated silanol-nest-containing delaminated zeolitic materials are unprecedented. The aforementioned delaminated silanol-nest-containing zeolites possess disordered stacking of thin zeolitic sheets (~2.5 nm) along the c-axis, and a high density of silanol nests on the external surface, which can incorporate heteroatoms via tetrahedral molecular recognition at the nest site, to form isolated tetrahedral heteroatom sites that are incorporated within the zeolite framework. The resulting structures may facilitate many Lewis-acid catalyzed reactions, especially those containing bulky molecules. The present novel synthesis is scalable and has significant potential impact to the fine chemical and pharmaceutical industries.

DETAILED DESCRIPTION OF THE INVENTION

Figure 1:
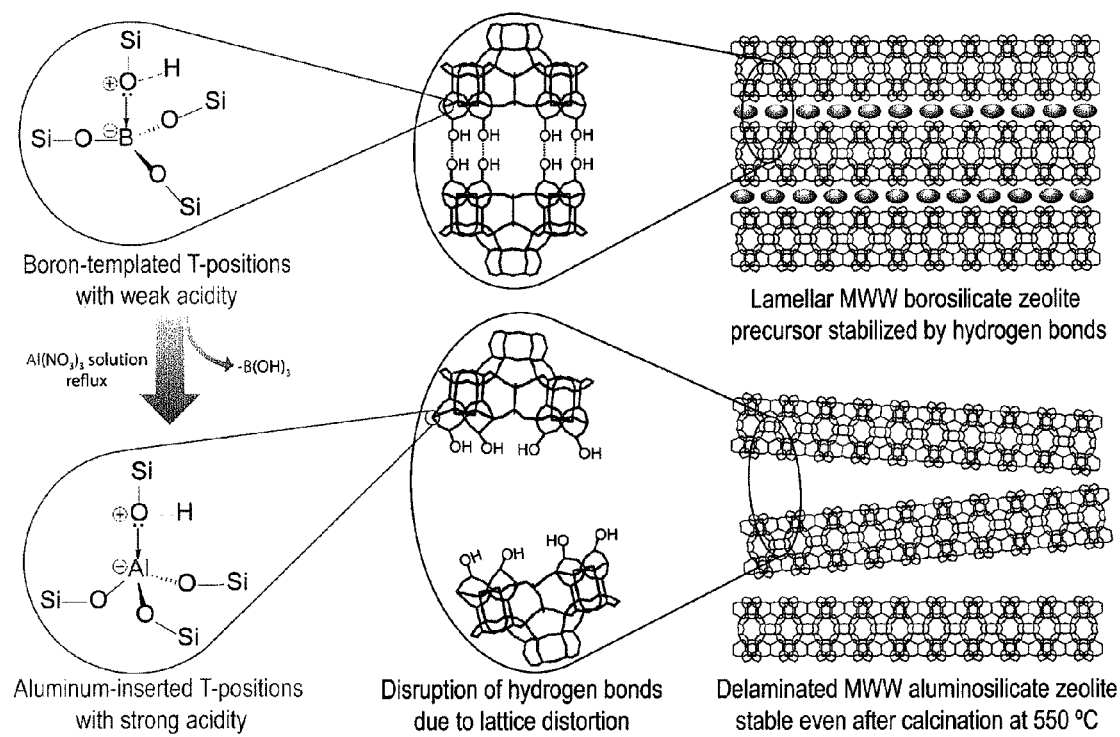
FIG. 1 shows a schematic representation of the surfactant-free exfoliation of a MWW-type borosilicate zeolite precursor into a delaminated aluminosilicate zeolite in a single step.

The present invention provides a new method for imparting greater accessibility into zeolitic materials. The method comprises delamination that does not require organic surfactants and sonication and can remarkably be accomplished in a single-step treatment. The process comprises exfoliating layered borosilicate zeolite precursors via disruption of hydrogen bonds between layers by treating with warm metal salt solutions. The exfoliation is achieved in a single step, for example, during treatment in warm $Al(NO_3)_3$ aqueous solution. During this treatment, interlayer hydrogen bonding in the layered zeolite precursor is permanently disrupted (i.e. persists even after calcination at 550° C.) via lattice distortion, which is induced by substitution of B for Al. Another single-step exfoliation example is that, during treatment of borosilicate zeolite precursors in warm $Zn(NO_3)_2$ aqueous solution at pH of ~1, the interlayer hydrogen bonding in the layered zeolite precursor is permanently disrupted, and accompanied by the formation of silanol nests induced by B removal from the framework. Within this context, silanol nests refers to a plurality of silanols arranged within a template that used to be occupied by B. The high surface area and silanol nests of the exfoliated zeolites persist even after calcination at 550° C.

Delamination refers to the peeling apart of layers in a layered zeolite precursor, by replacing microporosity in the interlayer region of such a material with much larger spacing between the layers. Delamination is often accompanied by an increase in the external surface area of the material, typically in the range of 1.1-10 fold, and preferably in the range of about 2-4 fold. In a preferable embodiment of this invention, delamination is not accompanied by amorphization of the zeolite framework; and, therefore, the increase in surface area is largely due to the increase in external surface area exposed rather than contributions from other phases such as amorphous phases.

In the present invention, a borosilicate layered zeolite precursor is delaminated. The borosilicate layered zeolite precursor is an oxide material comprising oxides of the formula $SiO_2$ and $B_2O_3$, wherein the atomic ratio of Si to B is less than 200. The borosilicate zeolite layered precursor contains organic templates. The topologies of the borosilicate layered zeolite precursor includes, but not limited to, MWW, FER, CDO, CAS, NSI, MFI, SOD, RWR, RRO, and AFO. In the borosilicate layered zeolite precursor, B atoms occupy at T-positions. The term T-position refers to any atoms which have tetrahedral coordination positions in the zeolite framework. A zeolite may have at least one type of T-position in its framework. The most abundant type of atoms at T-positions in any zeolite is usually Si. Heteroatoms (e.g., Al, B, Ga, and Fe) may be introduced to certain T-positions and the resulting zeolite may show Brønsted acidity which are able to facilitate acid catalysis. The acid catalysis refers to a chemical reaction which is catalyzed by an acid. On the other hand, heteroatoms (e.g., Ti, Sn, Zr, Mn, Hf, Nb, Ta, and V) may also be introduced to certain T-positions and the resulting zeolite may be able to promote oxidation catalysis. The oxidation catalysis include all chemical reactions in which atoms have their oxidation state changed. Oxidant and reductant must be involved in oxidation catalysis. The oxidant is the element or compound in the oxidation catalysis which accepts an electron from another species.

In the present invention, delamination is intentionally and simultaneously accompanied by formation of silanol nest and/or changes in the heteroatom composition of the zeolite, by contacting with a solution containing metal salt. Solution within the latter context refers to either a dissolved metal salt in a solvent or the neat metal salt, in the case of metal salts that are themselves intrinsically liquids under conditions of contacting. Preferred heteroatoms can be either B or Al, but are not limited to such and can also include many others such as Zn, Mn, among others. In this context, metal salt refers to any coordination of a metal cation with an anion including inorganic anions such as nitrate and chloride as well as organic anions such as acetate and citrate and organic ligands such as alkoxide, carboxylates, halides and alkyls. The term silanol nest refers to a structural defect consisting of one or more silanols within a localized area from which heteroatoms have been removed. The silanol nest is able to be replenished with a heteroatom by contacting with a reactive heteroatom metal precursor. The material before this replenishment may be a zeolite consisting of silanol nests and largely lacking heteroatoms. In such a zeolite in which heteroatoms are largely absent, a typical Si:heteroatom ratio may be more than 10, and may be preferentially larger than 20, and even more preferentially larger than 50. An even more preferential Si:heteroatom ratio in a zeolite that is largely absent of heteroatoms is larger than 100, and the most preferential Si:heteroatom ratio in a zeolite that is largely absent of heteroatoms is larger than 200. This ratio is not intended to limit in any way the practice of this invention when synthesizing a zeolite consisting of silanol nests that is largely absent of heteroatoms. The reactive heteroatom metal precursor refers to be, but not limited to Ti(O-n-Bu)$_4$, TiCl$_4$, Ti(O-i-Pr)$_4$ among others that can condense with ROH group to form Ti—OR connectivity. The replenishment of the silanol nest with a heteroatom as mentioned above, or the exchange of one type of heteroatom with another type of heteroatom in a zeolite framework is known as isomorphous substitution. These compounds are known in the art.

Similarly, reactive heteroatom metal precursors can be defined for other metals such as Zr, Sn, Cr, V, and are known in the art as compounds that condense with ROH groups to form M-OR connectivity in general where M represents a general metal.

The materials after delamination and, in a preferred embodiment, delamination and contact with a reactive heteroatom metal precursor, may be useful as made. Alternatively, they may be partially demetallated to afford a more active catalyst. Partial demetallation refers to removal of a portion of the heteroatoms within the catalyst, typically the portion that is bonded more weakly and, typically, this is the portion that is not as fully condensed to the zeolite framework. When applied to Al metal, the process of demetallation is termed dealumination. There are several preferred methods of dealumination, and this specification is not to be limited in any way based on the method of demetallation practiced. For example, it is well known in the art that dealumination can accomplished by either (i) a brief aqueous acid solution treatment (Barrer, R. M., Makki, M. B. (1964) Can J Chem 42:1481); (ii) steam treatment (Scherzer, J. The Preparation and Characterization of Aluminum Deficient Zeolite, "Catalytic Materials" ACS Symposium Series. 1984, 248:157-200); and (iii) ammonium fluorosilicate treatment (Breck, D. W., Blass, H., Skeels, G. W. (1985) U.S. Pat. No. 4,503,023, Union Carbide Corp).

The present process, therefore, prepares a delaminated aluminosilicate zeolite. The process comprises refluxing a MWW borosilicate zeolite precursor in an aluminum nitrate solution. FIG. 1 shows a schematic representation of the surfactant free exfoliation of a MWW-type borosilicate zeolite precursor into a delaminated aluminosilicate zeolite in a single step. Once recovered from solution, the delaminated aluminosilicate zeolite can be calcined.

One example of this approach employs a layered borosilicate zeolite precursor ERB-1P. The precursor is used to synthesize new delaminated zeolitic materials such as ERB-1del-135, which has a similar topology to previously described ITQ-2 and UCB-1, which are also based on MWW-type layered zeolite precursors. Heretofore this substitution has never been performed on a layered zeolite precursor, which has not been calcined and which therefore consists of a high amount of SDA remaining in the framework. The results demonstrate that this leads to removal of most of the piperidine SDA and delamination.

The resulting delaminated aluminosilicate zeolites are also unique in their disordered stacking of thin sheets along the c-axis. The zeolites also possess a high density of strong acid sites on the external surface. As a result, the delaminated aluminosilicate zeolites are particularly effective as a catalyst for acid-catalyzed reactions with hydrocarbons. The reaction would comprise contacting a hydrocarbon feed with the catalyst under suitable reaction conditions. The delaminated zeolites are suitable for reactions such as isomerization, alkylation, acylation, cracking or hydrolysis. The delaminated zeolite catalysts would be of particular use in reactions involving bulky hydrocarbon molecules.

Figure 12:
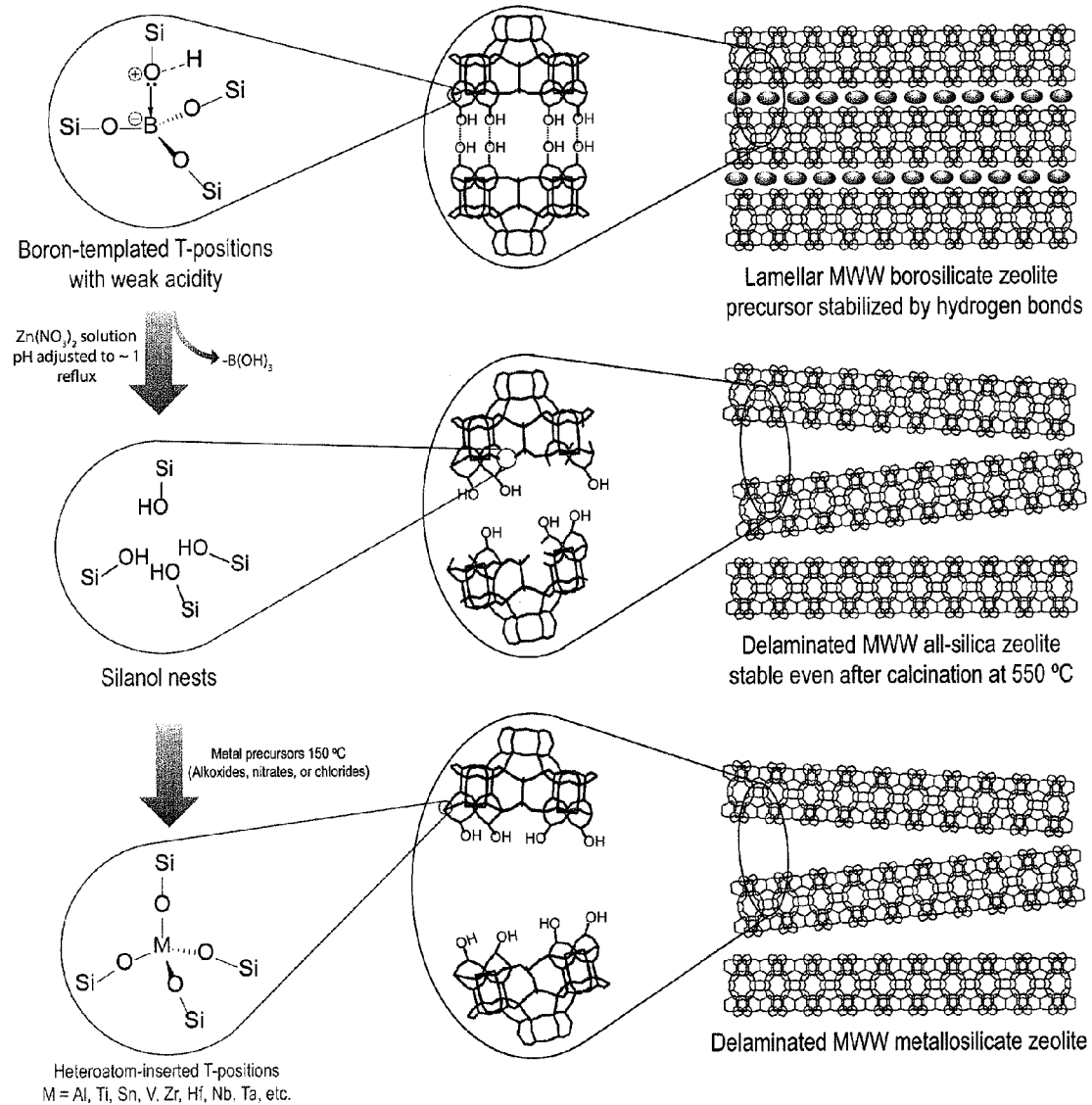
FIG. 12 shows a schematic representation of the surfactant-free exfoliation of a MWW-type borosilicate zeolite precursor into a delaminated silanols-nest-containing zeolite in a single step, as well as following steps to incorporate heteroatoms into the zeolite framework.

In another embodiment, the present process synthesizes a delaminated silanol-nest-containing zeolite. The process comprises refluxing a MWW borosilicate zeolite precursor in either a zinc nitrate or manganese nitrate solution. FIG. 12 shows a schematic representation of the one-step and surfactant-free exfoliation of a MWW-type borosilicate zeolite precursor into a delaminated zeolite, which possesses a high density of silanol nests on the external surface. Once recovered from solution, the delaminated silanol-nest-containing zeolite can be calcined and still maintains the large surface area. One example of this approach employs a layered borosilicate zeolite precursor ERB-1P. The precursor is used to synthesize new delaminated zeolite materials, such as ERB-1D, which are enriched with silanol nests. This delamination accompanied by simultaneous formation of silanol nest has not been performed on any layered zeolite precursor previously.

The following examples are being provided to better exemplify the present invention. The examples are not meant to be limiting, only illustrative.

EXAMPLES

Materials

All reagents used in zeolite synthesis, delamination and catalysis were of reagent grade quality and were used as-received. Acridine (97%, Sigma-Aldrich) was recrystallized in ethanol twice before titration.

Synthesis of ERB-1 Precursor (ERB-1P).

Synthesis of ERB-1P was performed according to previously described literature with minor modifications (see Millini, R.; Perego, G.; Parker, W. O.; Bellussi, G.; Carluccio, L. *Microporous Materials* 1995, 4, 221.) Typically, 2.40 g of NaOH (EMD Chemicals, 97%) and 6.18 g of $H_3BO_3$ (≥99.5%, Fisher Chemical) were dissolved in 30 mL of nanopure $H_2O$, and 12.8 g of piperidine (≥99.5%, purified by redistillation, Sigma-Aldrich). To this mixture, 9.0 g of $SiO_2$ (Aerosil® 200, Evonik-Degussa) and 0.10 g of see crystals (as-made ERB-1P, Si/B=11) were added. A white viscous gel was obtained after mixing with a spatula. The gel composition was $SiO_2$:0.33 $B_2O_3$:0.2 $Na_2O$:1.0 piperidine: 11.0 $H_2O$. The gel was subsequently transferred to a 125 mL Parr reactor equipped with a Teflon liner. The reactor was heated at 175° C. for 7~9 days without agitation. After cooling, the contents were poured into a filter and the precipitated solids were washed several times with water and then air-dried.

Synthesis of MCM-22P.

The zeolite was synthesized according to the literature method (see Maheshwari, S.; Jordan, E.; Kumar, S.; Bates, F. S.; Penn, R. L.; Shantz, D. F.; Tsapatsis, M. *Journal of the American Chemical Society* 2008, 130, 1507. Gel compositions were $SiO_2$:0.011 $Al_2O_3$:0.079 $Na_2O$:0.49 hexamethyleneimine:44 $H_2O$. The reaction was conducted in a convection oven at 135° C. for 11 days with tumbling of the reactor.

Synthesis of B-SSZ-70.

1,3-diisobutylimidazolium (SDA) hydroxide solution for the synthesis of B-SSZ-70 was prepared according to previously described literature (see Ogino, I.; Eilertsen, E. A.; Hwang, S.-J.; Rea, T.; Xie, D.; Ouyang, X.; Zones, S. I.; Katz, A. *Chemistry of Materials* 2013; and Archer, R. H.; Zones, S. I.; Davis, M. E. *Microporous and Mesoporous Materials* 2010, 130, 255.) Synthesis of B-SSZ-70 was performed according to previously published method (see Ogino, I.; Eilertsen, E. A.; Hwang, S.-J.; Rea, T.; Xie, D.; Ouyang, X.; Zones, S. I.; Katz, A. *Chemistry of Materials* 2013.) Gel compositions were $SiO_2$: 0.033 $B_2O_3$: 0.050 $Na_2O$:0.20 SDA:30 $H_2O$. The reaction was conducted at 150° C. for 1~2 weeks with tumbling of the reactor.

Delamination of ERB-1P with $Al(NO_3)_3$ Solution.

In a typical procedure, 1.0 g of zeolite precursor was added to 100 g of 0.4 N $Al(NO_3)_3$ aqueous solution in a 150 mL sealed thick-wall glass reactor with vigorous stirring. The mixture was heated at various temperatures, including 100, 135, 150 and 175° C. The resulting materials are denoted as ERB-1-del-100, ERB-1-del-150, and ERB-1-del-175, respectively. The solid products were collected on a filter, air-dried, and subsequently calcined at 550° C. for 5 h in air.

Delamination of ERB-1P with $Ga(NO_3)_3$ Solution:

In a typical procedure, 1.0 g of zeolite precursor was added to 100 g of 0.4N $Ga(NO_3)_3$ aqueous solution in a 150 mL sealed thick-wall glass reactor with vigorous stirring. The mixture was heated at 135° C. for 24 hours. The resulting delaminated material is denoted as ERB-1-del-Ga. This material was collected on a filter, air dried, and subsequently calcined at 550° C. for 5 h in air.

Delamination of ERB-1P with $Zn(NO_3)_2$ Solution:

In a typical procedure, 1.0 g of zeolite precursor and 4.0 g of $Zn(NO_3)_2 \cdot 6H_2O$ were added to 35 g of pH 1 $HNO_3$ solution in a 48 mL sealed thick-wall glass reactor with vigorous stirring. The mixture was heated at 135° C. for 24 hours. The resulting delaminated material is denoted as ERB-1D(Zn). This material was collected on a filter, washed with 50 mL deionized water for three times, and finally air-dried.

Delamination of ERB-1P with $Mn(NO_3)_2$ Solution:

In a typical procedure, 1.0 g of zeolite precursor and 4.0 g of $Mn(NO_3)_2 \cdot 4H_2O$ were added to 35 g of pH 1 aqueous $HNO_3$ solution in a 48 mL sealed thick-wall glass reactor with vigorous stirring. The mixture was heated at 135° C. for 24 hours. The resulting delaminated material is denoted as ERB-1D(Mn). This material was collected on a filter, washed with 50 mL deionized water for three times, and finally air-dried.

Synthesis of DTiZ-1:

In a typical procedure, 0.5 g of ERB-1D(Zn) or ERB-1D (Mn) was added to 1.0~4.0 mL of $Ti(n-OBu)_4$ in a 48 mL sealed thick-wall glass reactor with vigorous stirring. The mixture was heated at 25~175° C. for 10 min~5 hours. Then the temperature was lowered to 120° C., and 20 mL n-BuOH was added to the mixture. After vigorous stirring at 120° C. for 1 hour. The solid product was collected on a filter, washed with 20 mL n-BuOH for three times, then air-dried.

The resulting material is denoted as DTiZ-1. The resulting DTiZ-1 has a ratio of Si/Ti between 40 and 200 based on the details of the synthesis (i.e. longer contacting time of metal precursor with the delaminated zeolite and more forcing conditions such as increased temperature lead to more heteroatom incorporation).

Synthesis of DSnZ-1:

The procedure below describes a method of inserting Sn into a delaminated material consisting of silanol nests, using a Sn-containing reactive heteroatom metal precursor. In a typical procedure, 0.5 g of either ERB-1D(Zn) or ERB-1 (Mn) was added to 1.0 g~5.0 g of $SnCl_4 \cdot 5H_2O$ in a 48 mL sealed thick-walled glass reactor with vigorous stirring. The mixture was heated at 56~175° C. for 10 min~2 hours. Then the temperature was lowered to 120° C., and 20 mL of n-BuOH was added to the mixture. After vigorous stirring at 120° C. for 1 hour, the solid product was collected via filtration, and was washed with 20 mL of n-BuOH three times. The product was then air-dried. The resulting delaminated material incorporating Sn is denoted as DSnZ-1. The resulting DSnZ-1 has a ratio of Si/Sn between 40 and 200 based on the details of the synthesis (i.e. longer contacting time of metal precursor with the delaminated zeolite and more forcing conditions such as increased temperature lead to more heteroatom incorporation).

Synthesis of DZrZ-1:

The procedure below describes a method of inserting Zr into a delaminated material consisting of silanol nests, using a Zr-containing reactive heteroatom metal precursor. In a typical procedure, 0.5 g of either ERB-1D(Zn) or ERB-1 (Mn) was added to 1.0~4.0 ml of $Zr(n-OBu)_4$ in a 48 mL sealed thick-walled glass reactor with vigorous stirring. The mixture was heated at 25~175° C. for 10 min~5 hours. Then the temperature was lowered to 120° C., and 20 mL of n-BuOH was added to the mixture. After vigorous stirring at 120° C. for 1 hour, the solid product was collected via filtration, and was washed with 20 mL of n-BuOH three times. The product was then air-dried. The resulting delaminated material incorporating Sn is denoted as DZrZ-1. The resulting DZrZ-1 has a ratio of Si/Zr between 40 and 200, based on the details of the synthesis (i.e. longer contacting time of metal precursor with the delaminated zeolite and more forcing conditions such as increased temperature lead to more heteroatom incorporation).

Synthesis of DHfZ-1:

The procedure below describes a method of inserting Hf into a delaminated material consisting of silanol nests, using a Hf-containing reactive heteroatom metal precursor. In a typical procedure, 0.5 g of either ERB-1D(Zn) or ERB-1 (Mn) was added to 1.0~4.0 ml of $Hf(n-OBu)_4$ in a 48 mL sealed thick-walled glass reactor with vigorous stirring. The mixture was heated at 25~175° C. for 10 min~5 hours. Then the temperature was lowered to 120° C., and 20 mL of n-BuOH was added to the mixture. After vigorous stirring at 120° C. for 1 hour, the solid product was collected via filtration, and was washed with 20 mL of n-BuOH three times. The product was then air-dried. The resulting delaminated material incorporating Sn is denoted as DHfZ-1. The resulting DHfZ-1 has a ratio of Si/Hf between 40 and 200 based on the details of the synthesis (i.e. longer contacting time of metal precursor with the delaminated zeolite and more forcing conditions such as increased temperature lead to more heteroatom incorporation).

Synthesis of DNbZ-1:

The procedure below describes a method of inserting Nb into a delaminated material consisting of silanol nests, using a Nb-containing reactive heteroatom metal precursor. In a typical procedure, 0.5 g of either ERB-1D(Zn) or ERB-1 (Mn) was added to 1.0~4.0 ml of $Nb(OEt)_4$ in a 48 mL sealed thick-walled glass reactor with vigorous stirring. The mixture was heated at 25~175° C. for 10 min~5 hours. Then the temperature was lowered to 120° C., and 20 mL of n-BuOH was added to the mixture. After vigorous stirring at 120° C. for 1 hour, the solid product was collected via filtration, and was washed with 20 mL of n-BuOH three times. The product was then air-dried. The resulting delaminated material incorporating Sn is denoted as DNbZ-1. The resulting DNbZ-1 has a ratio of Si/Nb between 40 and 200 based on the details of the synthesis (i.e. longer contacting time of metal precursor with the delaminated zeolite and more forcing conditions such as increased temperature lead to more heteroatom incorporation).

Synthesis of DTaZ-1:

The procedure below describes a method of inserting Ta into a delaminated material consisting of silanol nests, using a Ta-containing reactive heteroatom metal precursor. In a typical procedure, 0.5 g of either ERB-1D(Zn) or ERB-1 (Mn) was added to 1.0~4.0 ml of $Ta(OEt)_4$ in a 48 mL sealed thick-walled glass reactor with vigorous stirring. The mixture was heated at 25~175° C. for 10 min~5 hours. Then the temperature was lowered to 120° C., and 20 mL of n-BuOH was added to the mixture. After vigorous stirring at 120° C. for 1 hour, the solid product was collected via filtration, and was washed with 20 mL of n-BuOH three times. The product was then air-dried. The resulting delaminated material incorporating Sn is denoted as DTaZ-1. The resulting DTaZ-1 has a ratio of Si/Ta between 40 and 200 based on the details of the synthesis (i.e. longer contacting time of metal precursor with the delaminated zeolite and more forcing conditions such as increased temperature lead to more heteroatom incorporation).

Synthesis of DVZ-1:

The procedure below describes a method of inserting V into a delaminated material consisting of silanols nests, using a V-containing reactive heteroatom metal precursor. In a typical procedure, 0.5 g of either ERB-1D(Zn) or ERB-1 (Mn) was added to 1.0~4.0 ml of $VO(O-i-Pr)_3$ in a 48 mL sealed thick-walled glass reactor with vigorous stirring. The mixture was heated at 25~175° C. for 10~5 hours. Then the temperature was lowered to 120° C. and 20 ml of n-BuOH was added to the mixture. After vigorous stirring at 120° C. for 1 hour, the solid product was collected via filtration, and was washed with 20 ml of n-BuOH three times. The product was then air-dried. The resulting delaminated material incorporating Sn is detected as DVZ-1. The resulting DVZ-1 has a ratio of Si/V between 40 and 200 based on the details of the synthesis (i.e. longer contacting time of metal precursor with the delaminated zeolite and more forcing conditions such as increased temperature lead to more heteroatom incorporation).

Dealumination of ERB-1-Del-135 with Nitric Acid

In a typical procedure, 1.0 g of ERB-1-del-135 was added to 20.0 g of 2 mol/L nitric acid aqueous solution in a 48 mL thick-walled glass reactor with vigorous stirring. The mixture was heated at 100° C. for 1 day. The resulting dealuminated materials is denoted as ERB-1-del-135'. This material was collected on a filter, air dried, and subsequently calcined at 550° C. for 5 h in air.

Acid Washing of DTiZ-1

In a typical procedure, 0.5 g of DTiZ-1 was added to 20.0 g of 2 mol/L nitric acid aqueous solution in a 48 mL thick walled glass reactor with vigorous stirring. The mixture was heated at 100° C. for 2 h. The resulting acid washed material is denoted as acid washed DTiZ-1W. This material was collected on a filter, air dried, and subsequently calcined at 550° C. for 5 h in air.

Acid washing of DSnZ-1

In a typical procedure, 0.5 g of DSnZ-1 was added to 20.0 g of 2 mol/L nitric acid aqueous solution in a 48 mL thick walled glass reactor with vigorous stirring. The mixture was heated at 100° C. for 2 h. The resulting acid washed material is denoted as acid washed DSnZ-1W This material was collected on a filter, air dried, and subsequently calcined at 550° C. for 5 h in air.

Friedel-Craft Acylation.

All chemicals were purchased from Sigma-Aldrich Co. Only the acetic anhydride was further purified with activated 4 A molecular sieves before use. Acylation reactions were carried out in a sealed 48 mL thick-wall glass tube with a magnetic stirrer (600 rpm) and heated under autogenous pressure in an oil bath at 120° C. with acetic anhydride (Ac$_2$O) as the acylating reagent and 1,2-dichloroethane as the solvent. Prior to use, 0.10 g of catalyst was activated in situ in air to 500° C. 1.1 mmol of 2MN, 1.1 mmol of Ac$_2$O, and an internal standard (1.1 mmol of dodecane) were dissolved in 10 mL of solvent and added to the vessel. Aliquots of the reaction mixture were sampled and analyzed by gas chromatography equipped with a FID detector (Agilent 6890) on a 30-m HP-1 column. The products were identified by comparing their retention time to 2,6-AMN and 1,2-AMN. The error in the experimental results was found to be in a range of ±3-4%.

Baeyer-Villiger Oxidation.

All chemicals were purchased from Sigma-Aldrich Co, and were used without further purification. Baeyer-Villiger oxidation was conducted in a sealed 48 mL thick-wall glass tube with a magnetic stirrer (600 rpm), which was heated under autogenous pressure in an oil bath at 60° C., with aqueous H2O2 (30.8 wt %, 0.5 mmol) as the oxidant and a ketone (0.5 mmol) as the reductant. Dodecane (0.5 mmol) is used as the internal standard. 1,4-dioxane (1.45 mL) is used as the solvent. Prior to use, the heteroatom-containing delaminated zeolite (0.66 mol % heteroatom with respect to ketone) was added to the reactants in vessel. Aliquots of the reaction mixture were sampled and analyzed by gas chromatography equipped with a FID detector (Agilent 6890) on a 30-m HP-1 column. The products were identified by comparing their retention time to the ketone reactant and the lactone product. The error in the experimental results was found to be in a range of ±3-4%.

Olefin Epoxidation.

All chemicals were purchased from Sigma-Aldrich Co. Cyclohenxene, 1-octene and octane were purified by distillation before use. Olefin epoxidation was carried out in a sealed 48 mL thick-wall glass tube with a magnetic stirrer (600 rpm) and heated under autogenous pressure in an oil bath at 60° C. with tert-butyl hydroperoxide (TBHP, 4.47 mmol) as the oxidant and an olefin (4.47 mmol) as the reductant. Nonane (0.5 mmol) is used as the internal standard. Octane (20 mL) is used as the solvent. Prior to use, DTiZ-1 (25 mg) was added to the reactants in vessel. Aliquots of the reaction mixture were sampled and analyzed by gas chromatography equipped with a FID detector (Agilent 6890) on a 30-m HP-1 column. The products were identified by comparing their retention time to the olefin reactant and the epoxide product. The error in the experimental results was found to be in a range of ±3-4%.

Results and Discussion

PXRD Characterization of Structural Change in Long-Range Order

Characterization.

Figure 2:
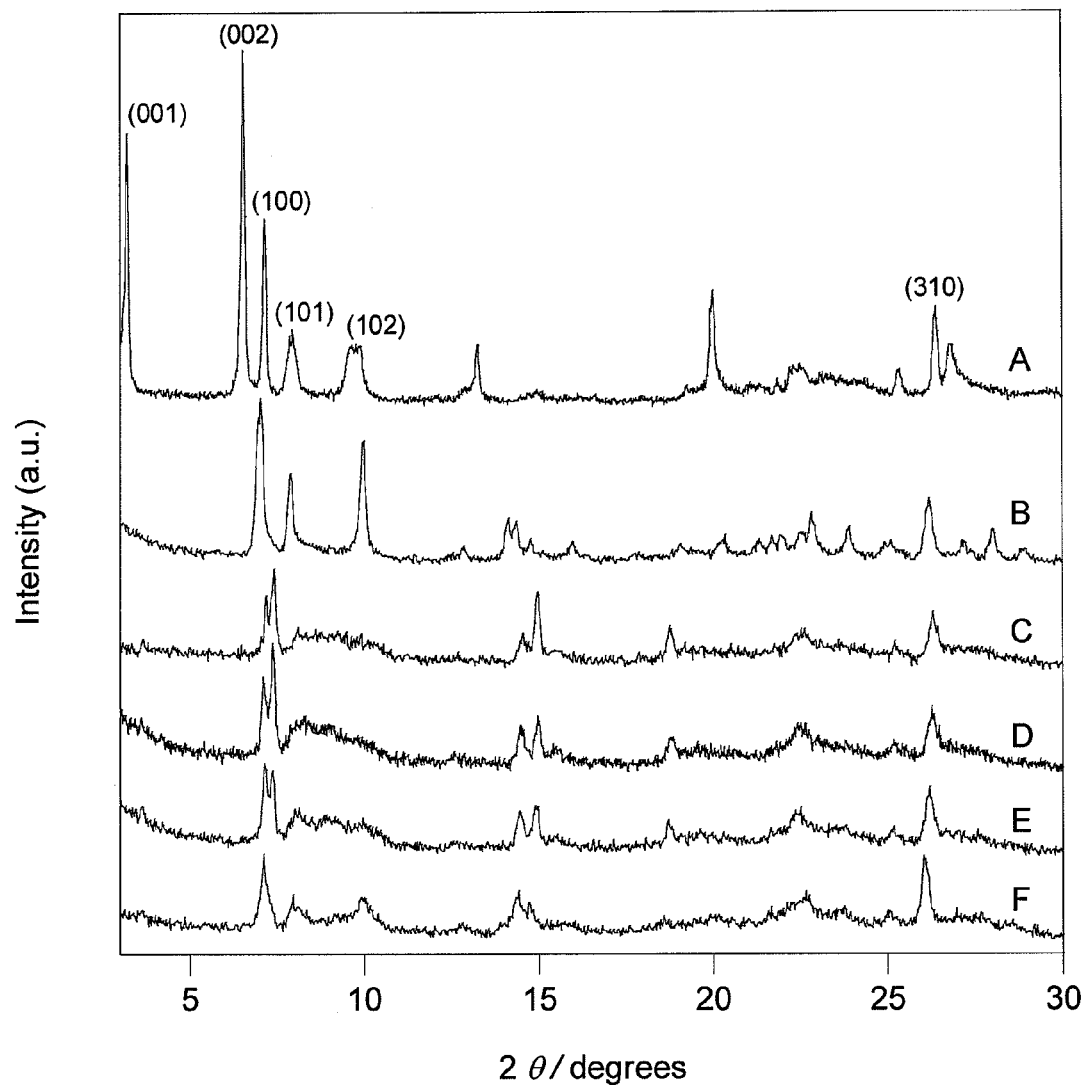
FIG. 2 shows a Powder X-ray diffraction patterns characterizing (A) ERB-1P, (B) ERB-1C, (C) ERB-1-del-100, (D) ERB-1-del-135, (E) ERB-1-del-150, and (F) ERB-1-del175.

Powder X-ray diffraction (XRD) patterns were collected on a Bruker GADDS D-8 diffractometer using a Cu Kα radiation. TEM. Nitrogen physisorption isotherms were measured on a Micromeritics ASAP2020 instrument at 77 K. Prior to measurement, samples were evacuated at 350° C. for 4 h. $^{29}$Si solid-state CP MAS NMR (CP contact time of 2 ms at 8 kHz sample spinning) spectra were measured using a Bruker Avance 500 MHz spectrometer with a wide-bore 11.7 T magnet and employing a 4-mm MAS probe (Bruker). The spectral frequency for the $^{29}$Si nucleus was 99.4 MHz. 29Si MAS NMR spectra were acquired after a 4 µs-90° pulse with application of a strong $^1$H decoupling pulse. The spinning rate was 12 kHz, and the recycle delay time was 300 s. PXRD patterns for the as-made, directly calcined, and delaminated ERB-1 materials are shown in FIG. 2. The low-angle peaks at 3.2° (d-spacing, 27.2 Å, reflection (001)) and 6.5° (dspacing, 13.6 Å, reflection (002)) represent the lamellar structure of ERB-1P, and the peaks at 7.1° (reflection (100)), 7.9° (reflection (101)), 9.7° (reflection (102)), and 26.3° (reflection (310)) are consistent with previously reported ERB-1P. Similar to previous observation by Millini et al., the intensities of reflections (001) and (002) decreased significantly after calcination of ERB-1P at 550° C., due to the structural changes along c-axis. (Millini, R.; Perego, G.; Parker, W. O.; Bellussi, G.; Carluccio, L. *Microporous Materials* 1995, 4, 221.) Reflection (002) likely shifted from 6.5° in ERB-1P to around 7.0° in ERB-1C, and merged with reflection (100) at 7.1° to make a slightly split peak centered at around 7.04° in ERB-1C, as shown in pattern B in FIG. 2. (Roth, W. J.; Dorset, D. L. *Microporous and Mesoporous Materials* 2011, 142, 32.) The reflections along a- and b-axes were essentially unchanged after direct calcination of ERB-1P.

Acridine adsorption was performed at room temperature. Approximately 3.0 mg of sample was placed in a 20 mL vial, and dried at 175° C. in oven for 4 h. After cooling, 2 mL of 500 µmol/L of acridine in hexane solution was added to the vial with a pipette (Eppendorf). The H-form zeolite sample should immediately turn green upon adding of acridine. The mixture was slightly agitated by hand, and was allowed to sit on the bench for 30 min. Then the mixture was filtered with a 0.2 μm syringe filter to remove the solids, and sampled for analysis by UV-vis spectrometry. The disappearance of acridine from solution, which is due to the adsorption of acridine on the zeolite external surface, was calculated from the difference between the absorption at 355 nm before and after titration. Fourier-transform infrared (FT-IR) spectra of zeolite pellets was recorded on a Nicolet 6700 FT-IR spectrometer in 2 cm$^{-1}$ resolution. The zeolite pellets were dried at 500° C. in vacuo for 2 h, and then transferred to an air-tight stainless steel IR cell with KBr windows (In-Situ Research Instruments) in glovebox, so that the pellets were not exposed to any moisture. Elemental analysis was performed at Galbraith Laboratories.

Delamination of ERB-1P from isomorphous substitution of Al into the ERB-1 framework caused the structural changes along both c-axis and a-b plane, as shown in patterns C, D, E, and F in FIG. 2. Clearly, reflections (001) and (002) shifted to 3.58° and 7.08°, respectively, with a significant reduction in intensity due to the loss of long-range order along c-axis. The similar changes were observed by Millini et al. in the ERB-1 calcined at 250° C. (Millini, R.; Perego, G.; Parker, W. O.; Bellussi, G.; Carluccio, L. *Microporous Materials* 1995, 4, 221. Interestingly, reflection (100) shifted from 7.1° (d-spacing, 14.3 Å) in ERB-1P to 7.4° (d-spacing, 13.8 Å) in the delaminated ERB-1 materials, indicating there is a contraction along a-axis, probably due to the distortion from the substitution of B by Al.

More importantly, the sharp peaks for reflections (101) and (102) in both ERB-1P and ERB1C were no longer observed. Instead, a broad band between 8 and 11° due to overlapping of reflection (101) and (102) was clearly observed. It has been proposed that simple visual examination of this broad band is considered an important approach to evaluate the efficiency of delamination. In FIG. 2, one can see that reflections (101) and (102) in pattern C, D, E, and F are much more collapsed than those in pattern A and B. Therefore, the delaminated ERB-1 materials should have large portion of layers which are not well aligned. In addition, ERB-1-del-135 (pattern D) is expected to have better layer-to-layer misalignment than ERB-1-del-175 (pattern F).

Figure 13:
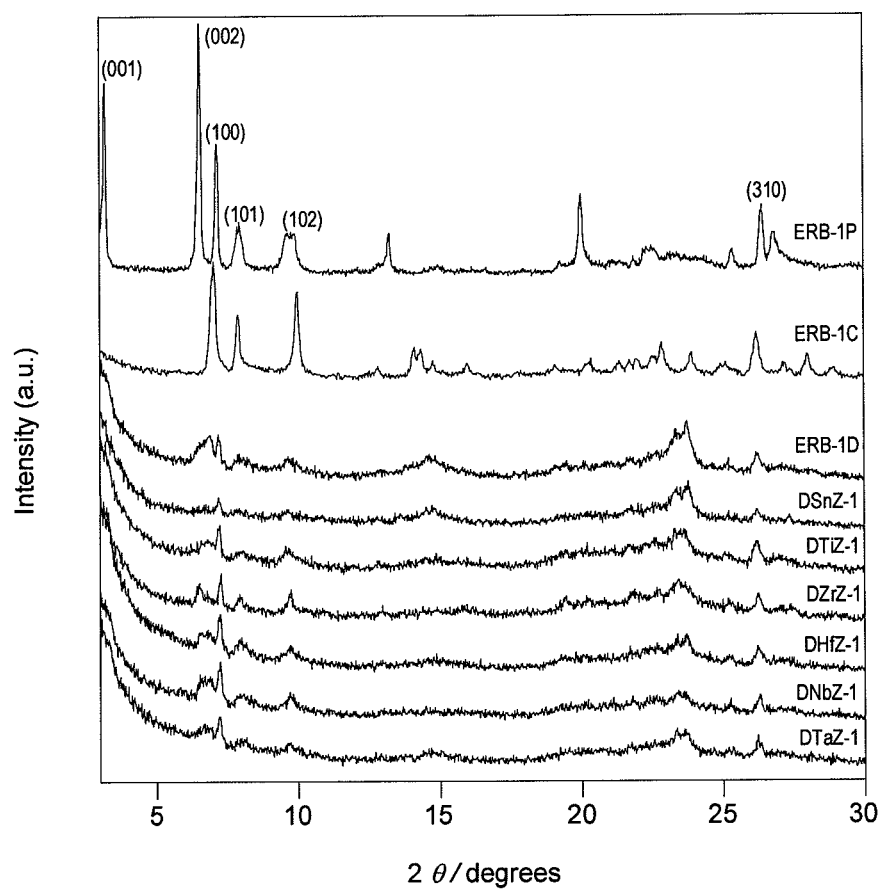
FIG. 13 shows powder X-ray diffraction patterns characterizing ERB-1P, ERB-1C, ERB-1D, DSnZ-1, DTiZ-1, DZrZ-1, DHfZ-1, DNbZ-1, and DTaZ-1.

Delamination of ERB-1P is accompanied by the disruption of hydrogen bonding and the formation of silanol nests caused by structural changes along both c-axis and a-b plane, as shown in patterns for ERB-1D, DSnZ-1, DTiZ-1, DZrZ-1, DHfZ-1, DNbZ-1, and DTaZ-1 in FIG. 13. Clearly, both reflections (001) and (002) are broadened and weakened significantly due to the loss of long-range order along c-axis. The (101) and (102) reflections show significant reduction in their intensity which is caused by the disordering along c-axis. Therefore, the delaminated ERB-1 materials should have large portion of layers which are not well aligned.

Figure 3:
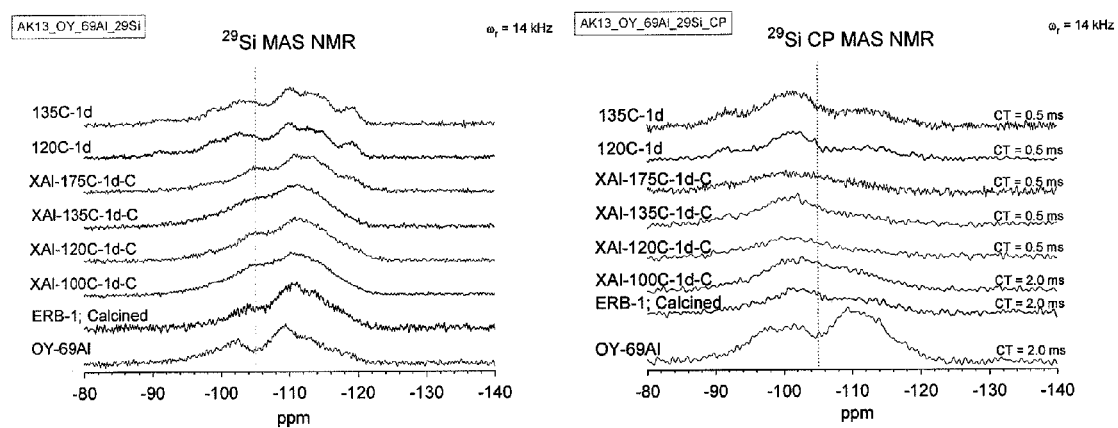
FIG. 3 shows $^{29}Si$ MAS and $^{29}Si$ CP MAS NMR data characterizing (A) ERB-1C, (B) ERB-1-del-100, (C) ERB-1-del-135, (D) ERB-1-del-150, and (E) ERB-1-del-175.

NMR Characterization of Local Structure $^{29}$Si MAS and $^{29}$Si CP MAS characterizing as-made, directly calcined, and delaminated ERB-1 materials in FIG. 3 show the entire absence of a $Q^2$ resonance at approximately −90 ppm, suggesting a lack of amorphization of the zeolite framework in all samples. The peaks are overall broad due to the low Si/B ratios in these samples. The comparison between $^{29}$Si MAS and $^{29}$Si CP MAS clearly shows peaks stand out in $^{29}$Si CP MAS spectra due to the presence of silanol groups, and the −101 ppm peak becomes stronger than peaks near at −105 ppm. The case is opposite for the $^{29}$Si MAS spectra, suggesting the peak at −105 ppm appeared stronger than that at −101 ppm. Therefore, the peaks at and higher than −105 ppm are assigned to $Q^4$ region, and the peaks below −105 ppm to $Q^3$ region.

The specific assignments of $Q^3$ and $Q^4$ resonances, i.e., −94.8 ppm ($Q^3$), −100.9 ppm ($Q^3$), −105.2 ppm ($Q^4$), −110.3 ppm ($Q^4$), −113.1 ppm ($Q^4$), −116.5 ppm ($Q^4$), and −119.5 ppm ($Q^4$), are referenced from the previously published data for as-made ITQ-1. Spectral fitting was conducted on the $^{29}$Si MAS spectra, and the $Q^3/Q^4$ ratios were calculated to evaluate the efficiency of delamination. Since a higher degree of delamination is achieved, a higher $Q^3/Q^4$ ratio is expected. All delaminated ERB-1 samples show higher $Q^3/Q^4$ ratios than ERB1C, and ERB-1-del-135 shows higher $Q^3/Q^4$ ratios than ERB-1-del-100 and ERB-1-del-175, suggesting that the delamination at 135° C., for example, in the range of from about 125145° C., leads to better layer separation than the delamination at 100 and 175° C. These results are consistent with the PXRD analysis.

Figure 4:
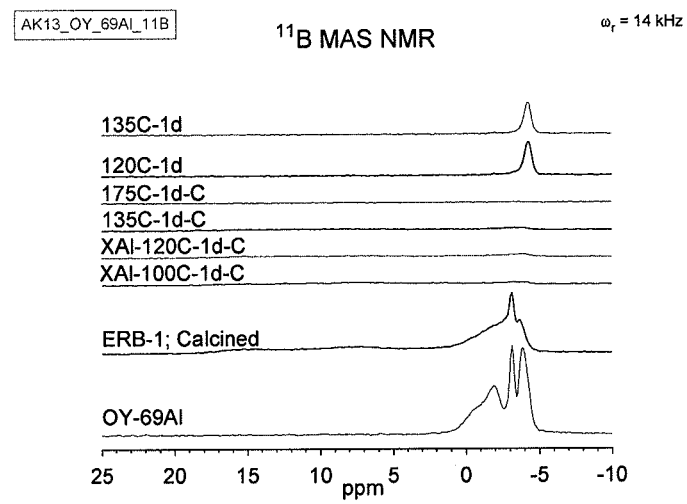
FIG. 4 shows $^{11}B$ MAS NMR data characterizing (A) ERB-1C, (B) ERB-1-del100, (C) ERB-1-del-135, (D) ERB-1-del-150, and (E) ERB-1-del-175.

$^{11}$B MAS NMR spectra of the as-made, directly calcined, and delaminated ERB-1 materials are shown in FIG. 4. $^{11}$B MAS NMR resonances that are relatively narrow in the −5~0 ppm range can be assigned to tetrahedrally coordinated boron sites (B[4]) in the T positions. Broad resonances between 20 and 0 ppm are due to the trigonally coordinated boron sites (B[3]), and the broad line shape downfield (10-17 ppm) was interpreted as a formation of extra-framework B[3] species which bear no B—O—Si bonds, such as B(OH)$_3$. (Hwang, S. J.; Chen, C. Y.; Zones; S. I. *Journal of Physical Chemistry B* 2004, 108, 18535; and Fild, C.; Shantz, D. F.; Lobo, R. F.; Koller, H. *Physical Chemistry Chemical Physics* 2000, 2, 3091.) ERB-1P have at least three major overlapping resonances (centered at −1.5, −3.0, and −4.0 ppm, respectively) for B[4] sites between −5 and 0 ppm, and no B[3] sites can be observed. One can conclude that the B atoms are located in several different T positions, but it is difficult to assign the exact location of each B[4] type at this stage. ERB-1C has different distributions of B[4] sites from ERB-1P. Notably, the peaks at −1.5 and −4.0 ppm decreased significantly, and there are two broad peaks (centered at 7 and 15 ppm, respectively) emerged due to possible formation of framework B[3] sites and extra-framework B[3] sites, respectively. The formation of framework B[3] is likely due to the dehydration of watercoordinated B[4] or de-coordination of piperidine-coordinated B[4] species during calcination. The emergence of extra-framework B[3] sites is probably due to deboronation induced by a mild hydration during calcination. Delamination in acidic Al(NO$_3$)$_3$ solution (pH≈2) removed almost all B in the structure, thus no clear signal of B was observed in $^{11}$B MAS NMR, which is consistent with the Si/B ratios from elemental analysis listed in Table 1.

Figure 5:
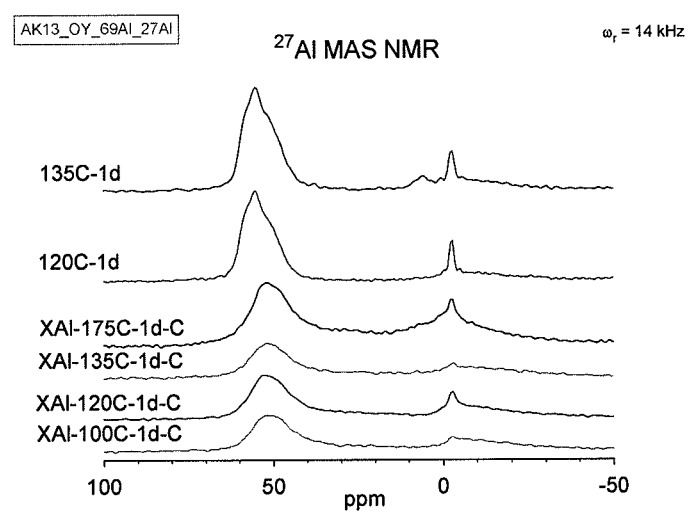
FIG. 5 shows $^{27}Al$ MAS NMR data characterizing (A) ERB-1C, (B) ERB-1-del100, (C) ERB-1-del-135, (D) ERB-1-del-150, and (E) ERB-1-del-175.

Isomorphous substitution of B by Al in calcined borosilicate zeolites via postsynthetic treatment with Al(NO$_3$)$_3$ solution were demonstrated previously. In this work, ERB-1P was treated directly with Al(NO$_3$)$_3$ solution at various temperatures without prior calcination to remove the SDA, piperidine. $^{27}$Al MAS NMR spectra of the delaminated ERB1 materials are shown in FIG. 5. $^{27}$Al MAS NMR resonance at about 50 ppm is assigned as framework tetrahedrally coordinated Al species (Al[4]), whereas the resonance at around 0 ppm is assigned as (Al[6]). The elemental analysis results, listed in Table 1 below, show that ERB-1-del-100 (Si/B=18) and ERB-1-del-135 (Si/B=15) reached partial lattice substitution of B by Al, probably because that steric effects prevent Al(H$_2$O)$_6^{3+}$ cations penetrating into 10MR at such temperatures, and only the silanol nests located at surface could be reinserted with Al. ERB-1-del-100 and ERB-1-del-135 both show their Al sites almost exclusively as tetrahedrally coordinated species (Al[4]). Interestingly, ERB-1-del-175 (Si/Al=10 vs. Si/B=11 in ERB-1P) reached almost complete lattice substitution of B by Al, however, it shows a strong and broad band centered at 0 ppm due to the resonance for Al[6], suggesting that significant amount of Al might just be partially anchored as Al[6] instead of forming Al[4] in framework. The high amount of Al[6] in ERB-1-del-175 again suggests that delamination at 135° C. is probably cleaner and more efficient that at 175° C.

Figure 14:
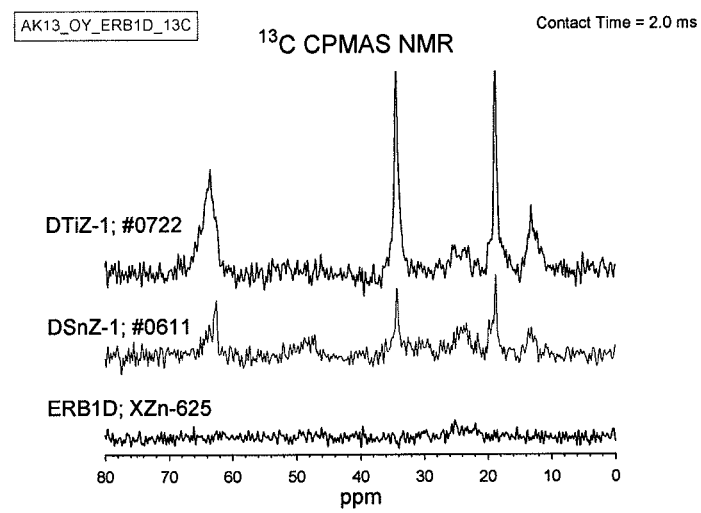
FIG. 14 has $^{13}C$ MAS NMR data characterizing ERB-1D, DSnZ-1, and DTiZ-1.

$^{13}$C MAS NMR spectra for ERB-1D, DSnZ-1 and DTiZ-1 are shown in FIG. 14. It is clear from the $^{13}$C MAS NMR that there is some organic residue in DSnZ-1 and DTiZ-1, whereas there is none in ERB-1D. The absence of organic residue in ERB-1D is due to the extraction of organic (piperidine) by acidic $Zn(NO_3)_2$ aqueous solution. The chemical shifts of the $^{13}$C NMR spectra, i.e., 13.4, 20.2, 35.2, and 61.4 ppm, are consistent with the presence of n-butoxy groups, which suggest that n-butoxy groups are grafted to the surface during re-insertion of Sn and Ti heteroatoms. Such a reaction is expected based on known condensation of n-butanol released from the metal butoxides with corresponding silanol function groups on the zeolite external surface.

Figure 15:
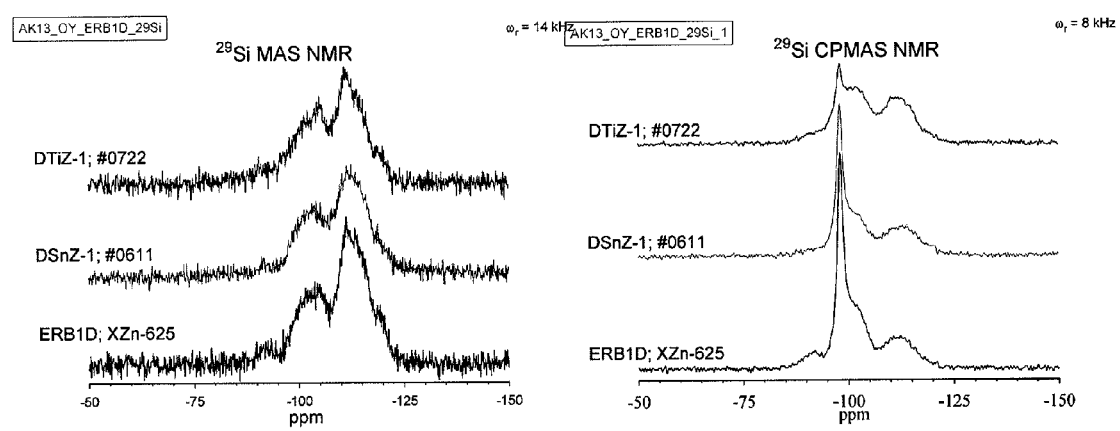
FIG. 15 has $^{29}Si$ MAS and $^{29}Si$ CPMAS NMR data characterizing ERB-1D, DSnZ-1 and DTiZ.

$^{29}$Si MAS and $^{29}$Si CPMAS NMR spectra for ERB-1D, DSnZ-1 and DTiZ-1 are shown in FIG. 15. The $Q^3$ Si peak at −98 ppm and its broad shoulder on the right side is most likely for silanol nests. As the silanol nests in ERB-1D are replenished by Sn or Ti heteroatom, such peak at −98 ppm becomes significantly smaller.

Figure 6:
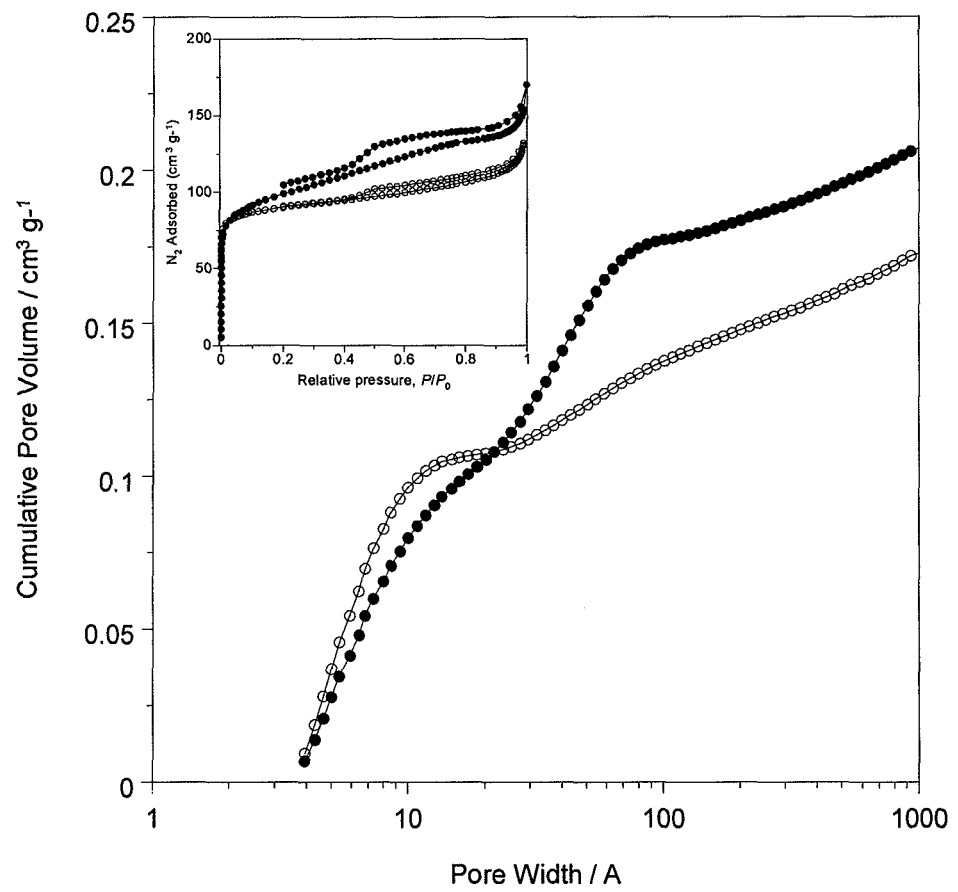
FIG. 6 shows $N_2$ NLDFT cumulative pore volume plots for (○) ERB-1C and (●) ERB-1-del-135. The inset shows the corresponding $N_2$ adsorption isotherms

Texture Analysis by $N_2$ Physisorption $N_2$ adsorption-desorption isotherms characterizing ERB-1C and ERB-1-del-135 are shown in FIG. 6. Table 1 below lists micropore and mesopore volume, as well as external surface areas, as determined by t-plot method. ERB-1-del-135 and ERB-1-del-150 show significantly lower micropore volume, higher mesopore volume, and higher external surface areas, relative to the corresponding calcined 3D zeolites, ERB-1C and ERB-1C-Al. On the other hand, ERB-1-del-100 does not show too much different micropore and mesopore volume, as well as external surface area, comparing to the corresponding 3D zeolites.

Interestingly, ERB-1-del-175 show significantly smaller micropore volume (0.08 cm$^3$/g vs. 0.12 cm$^3$/g for ERB-1C) than the 3D zeolites, but its external surface area is even slightly lower than the 3D zeolites. The decreased micropore volume in ERB-1-del-175 is likely due to the pore blockage by large amount of partially anchored Al[6] species. Therefore, it is clear that the high efficient delamination of ERB-1P by isomorphous substitution of B by Al must be conducted at a proper temperature range, which is presumably around 135° C., for example, in the range of from about 125-145° C.

Figure 16:
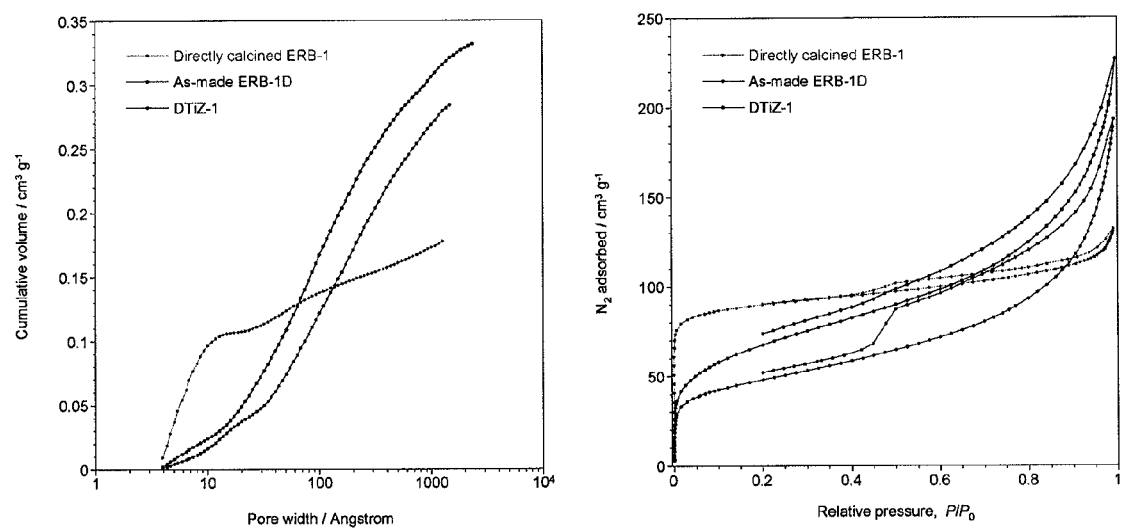
FIG. 16 has $N_2$ NLDFT differential pore volume plots over pore width distributions (left) and isotherm profile (right) for ERB-1C, ERB-1D and DTiZ-1.

FIG. 16 shows $N_2$ NLDFT differential pore volume plots over pore width distributions as well as the $N_2$ physisorption isotherm profile for ERB-1C, ERB-1D and DTiZ-1. It is clear that DTiZ-1 ($V_{micro}$=0.04 cm$^3$/g, Sext=171 m$^2$/g) and ERB-1D ($V_{micro}$=0.03 cm$^3$/g, Sext=122 m$^2$/g) have significantly smaller micropore volume and higher external surface area relative to ERB-1C ($V_{micro}$=0.12 cm$^3$/g, Sext=53 m$^2$/g).

DR-UV Spectroscopy

Figure 17:
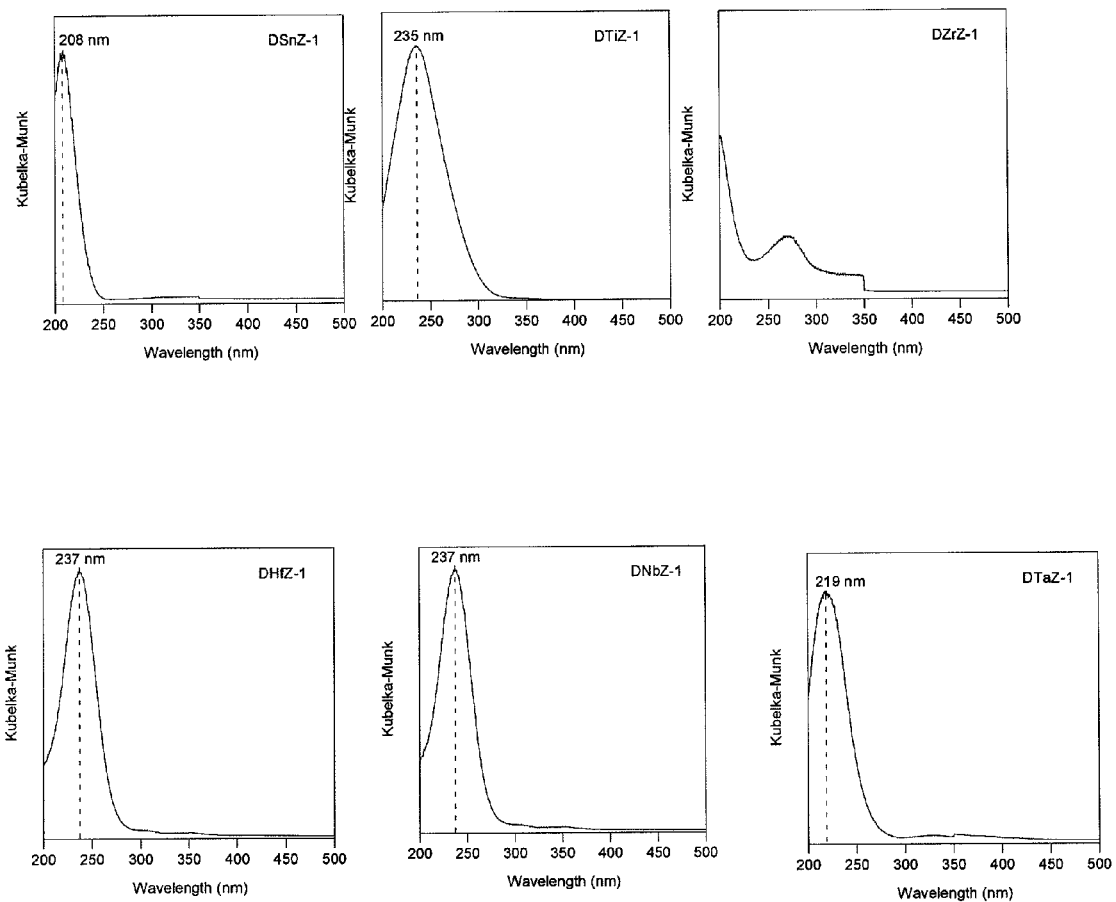
FIG. 17 shows DR-UV spectroscopy characterizing DSnZ-1, DTiZ-1, DZrZ-1, DHfZ-1. DNbZ-1, and DTaZ-1.

FIG. 17 Shows DR-UV spectroscopy data characterizing DSnZ-1, DTiZ-1, DZrZ-1, DHfZ-1, DNbZ-1, and DTaZ-1. These data show that all of these heteroatom-containing delaminated zeolites have isolated heteroatoms located in tetrahedral coordination in zeolitic framework. No bulk metal oxide is observed, since this would be consistent with lower-energy bands and edge energies, which are absent from all spectra.

Figure 10:
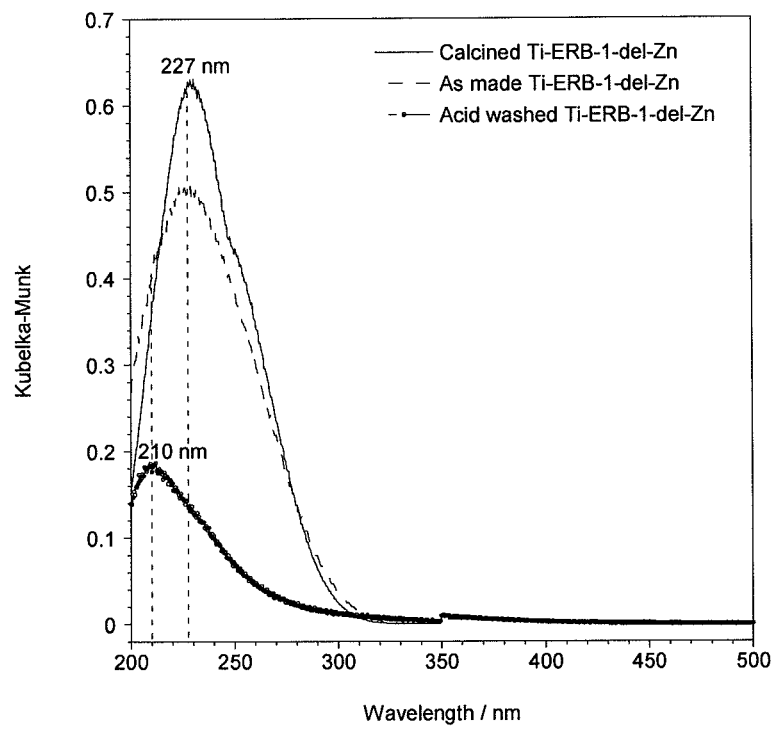
FIG. 10 shows diffuse-refluctance UV spectroscopy characterization of Ti-ERB-1-del-Zn materials.

DR-UV spectra for as-made DTiZ-1, calcined DTiZ-1, and acid washed DTiZ-1 are shown in FIG. 10. The as-made DTiZ-1 shows a peak centered at 227 nm and free of anatase phase. After calcination, there is essentially no change in the DR-UV spectrum, which suggests that no aggregation occurred. Acid washing (excess 2 N HCl at 100° C. for 2 h) led to a blue-shift of the peak from 227 nm to 210 nm, and a significant reduction of the DR-UV absorption band. Some of the tetrahedral Ti sites located at certain T-positions corresponding to the 227 nm adsorption band may be removed by acid washing, whereas the Ti sites corresponding to 210 nm still remain in the zeolite framework.

Quantification of Acid Sites by Acridine Adsorption

To confirm the framework Al-containing ERB-1 materials are in H-form, and measure the density of accessible acid sites on zeolites, acridine adsorption was explored in liquid phase as a new and fast base titration method. Acridine is structurally related to anthracene with one of the central CH group replaced by nitrogen. Acridine is a weak base with a pKa of 5.6, which is similar to that of pyridine. Acridine is not able to be adsorbed on silanol groups (on Aerosil® 200, pKa≈7) in hexane solution at room temperature, whereas pyridine is adsorbed strongly. Their different behaviors towards silanol groups could be explained as that acridine has much weaker polarity than pyridine due to its additional two benzene rings. Therefore, using acridine to titrate acid sites could avoid the error due to affinity between probe molecules and silanol groups, and such a simple liquid-phase titration at room temperature is much more convenient than the conventional vapor-phase titration by pyridine at elevated temperature (>120° C.). The mechanism of the titration of acid sites by acridine is depicted in Scheme 1:

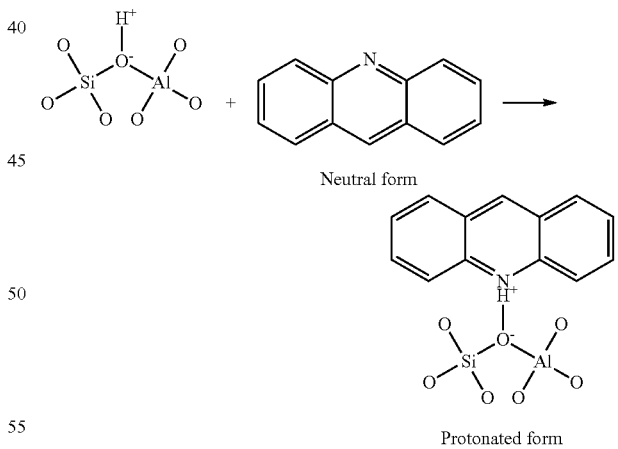

Scheme 1. Titration of Brønsted acid sites by acridine in solution.

Neutral form

Protonated form

The titration results of the as-made, calcined, and delaminated ERB-1 materials are listed in Table 1 below ERB-1P and ERB-1C do not show any uptake of acridine because the acidity of B sites are too weak. ERB-1C-Al (Si/Al=135) is a 3D zeolite made with postsynthetic isomorphous substitution of B by Al, which only has framework Al sites located on its surface, and an uptake of 75 μmol/g of acridine was achieved. H-MCM-22 (Si/Al=27) has higher density of Al sites than ERB-1C-Al, however, it only has almost the same amount of acridine adsorption. Presumably, acridine molecule is too large to enter 10MR, and only the surface acid sites can be titrated. The value of acridine adsorption is thus considered as another tool to evaluate the efficiency of delamination. ERB-1-del-135 has the highest value of acridine adsorption, 168 µmol/g, among all the delaminated ERB-1 materials, suggesting that delamination at about 135° C. has highest efficiency.

TABLE 1

Results from chemical analysis of as-made materials and nitrogen physisorption measurement of calcined materials.

| Sample | Si/B ratio | Si/Al ratio | $V_{micro}{}^a$ (cm³/g) | $V_{meso}{}^b$ (cm³/g) | $S_{ext}{}^c$ (m²/g) | Uptakes of Acridine$^d$ (µmol/g) |
|---|---|---|---|---|---|---|
| ERB-1P | 11 | n/a | n/a | n/a | n/a | 0 |
| ERB-1C | 10 | n/a | 0.12 | 0.04 | 53 | 0 |
| ERB-1C-Al | n/a | 135 | 0.12 | 0.04 | 54 | 75 |
| ERB-1-del-100 | n/a | 18 | 0.11 | 0.05 | 71 | 164 |
| ERB-1-del-135 | n/a | 15 | 0.09 | 0.08 | 133 | 168 |
| ERB-1-del-150 | n/a | 16 | 0.06 | 0.08 | 129 | 122 |
| ERB-1-del-175 | n/a | 10 | 0.08 | 0.03 | 30 | 47 |
| H-MCM-22 | n/a | 27 | 0.14 | 0.04 | 56 | 80 |

$^a$Micropore volume determined by t-plot method;
$^b$Mesopore (between 1 and 10 nm in diameter) volume determined by NLDFT method;
$^c$External surface area;
$^d$The titration of acridine was conducted at room temperature. 3 mg of zeolite sample was treated with 2 mL of 500 µmol/L acridine/hexane solution. The disappearance of acridine was checked by liquid phase UV-Vis spectroscopy.

FT-IR Characterization

Figure 7:
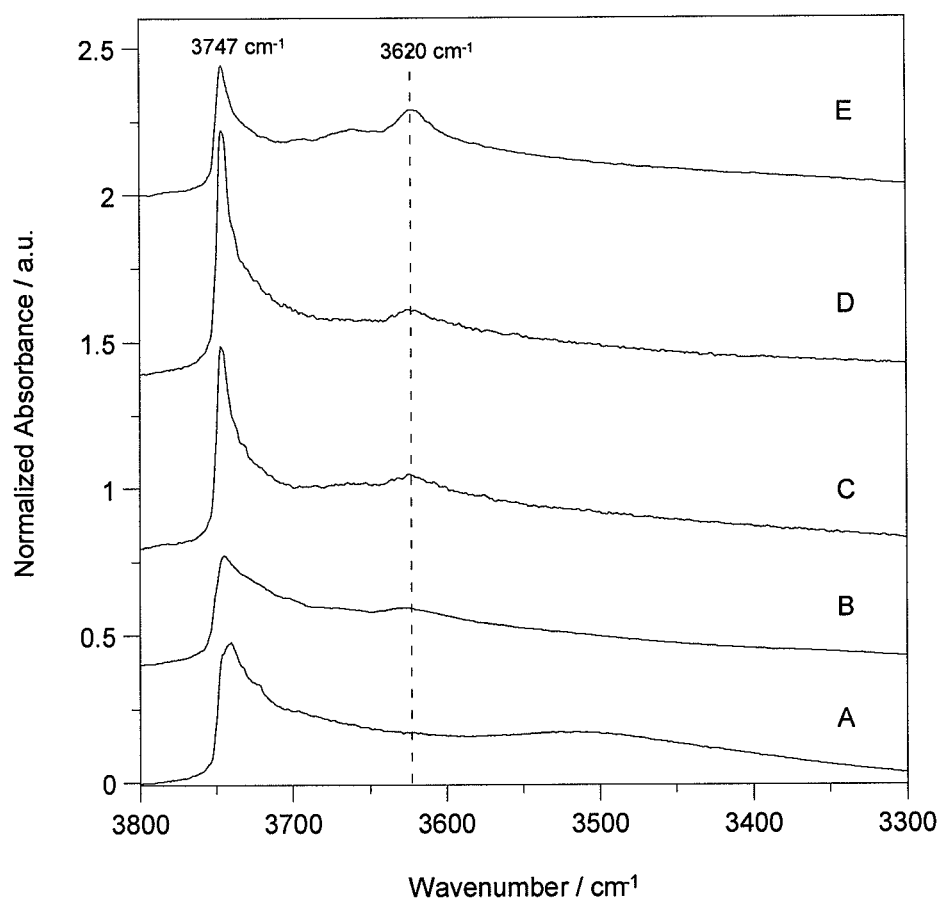
FIG. 7 shows Fourier transform infrared spectroscopy characterizing ERB-1 related materials. (A) ERB-1C-Al, (B) ERB-1-del-100, (C) ERB-1-del-135, (D) ERB-1-del-150, and (E) ERB-1-del-175.

FT-IR spectra (normalized with respect to weight) characterizing the silanol groups on the 3D and delaminated ERB-1 materials are shown in FIG. 7. The peak at 3747 cm$^{-1}$ is assigned to the isolated SiOH species. Delamination leads to cleavage of the 10MR between layers, therefore, higher density of isolated SiOH species are present. ERB-1-del-135 and ERB-1-del-150 show stronger and sharper peak at 3747 cm$^{-1}$ than 3D zeolite and the delaminated ERB-1 prepared at lower (~100° C.) and higher temperatures (~175° C.), again suggesting that delamination at 135° C. and 150° C. have better results. The tailing at lower frequencies (3730-3720 cm$^{-1}$) was observed on each sample, and it could be due to either silanols on the internal surface or the perturbed silanol groups. The peak at around 3620 cm$^{-1}$ is due to Brønsted acid sites, Si(OH)Al. The presence of the peak at 3620 cm$^{-1}$ confirms the success in isomorphous substitution of B by Al. ERB-1-C—Al (spectrum A) does not show noticeable peak at 3620 cm$^{-1}$, instead, it has strong absorbance band at 3700 and 3500 cm$^{-1}$ due to internal silanol groups from the framework defects, or silanol nests. The negligible amount of Brønsted acid sites in ERB-1-C—Al is believed because that Al $(H_2O)_6{}^{3+}$ cation is too large to enter the 10MR, thus only the external surface of the 3D zeolite ERB-1-C—Al have reinserted Al. On the other hand, $H_3O^+$ generated from hydrolysis of $Al(NO_3)_3$ are able to penetrate 10MR to leach out framework B and form silanol nests. ERB-1-del-135 and ERB-1-del-150 have a clean peak at 3620 cm$^{-1}$, confirming the success in generating strong Brønsted acid sites and the tetrahedral coordination environment for Al. ERB-1-del-175 (spectrum E) shows the strongest peak at 3620 cm$^{-1}$ among all delaminated samples, due to its low Si/Al of 10. Interestingly, ERB-1-del-175 also has an absorption band at 3700-3650 cm$^{-1}$, which is often assigned to hydroxyls linked to extraframework Al species, e.g., AlOH group, and it is consistent with the presence of strong resonance at 0 ppm for Al[6] in $^{27}$Al MAS NMR.

Figure 11:
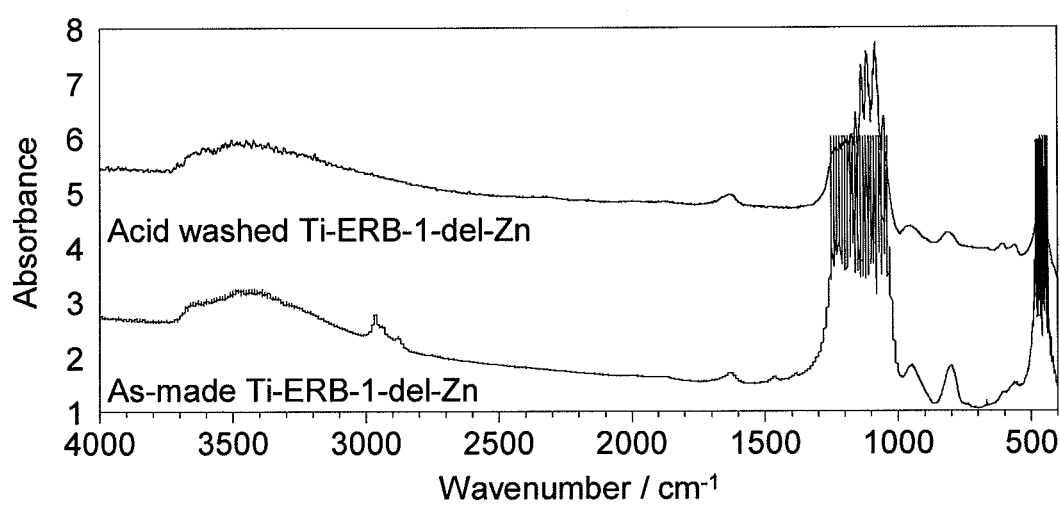
FIG. 11 shows FT-IR spectroscopy characterization of Ti-ERB-1-del-Zn materials.

FIG. 11 shows FT-IR spectroscopy characterization of DTiZ-1 before and after acid washing. Both materials show a peak at ~960 cm$^{-1}$ due to framework Ti(—O—Si)$_4$ in tetrahedral or nearly tetrahedral coordination, similar peak was reported for TS-1 previously (Ricchiardi, G.; Damin, A.; Bordiga, S.; Lamberti, C.; Spano, G.; Rivetti F.; Zecchina, A. J. Am. Chem. Soc., 2001, 121, 11409). The as-made DTiZ-1 has a broad stretching band between 2800~3000 cm$^{-1}$ due to the butoxy groups, after acid washing, this peak is removed completely.

Figure 18:
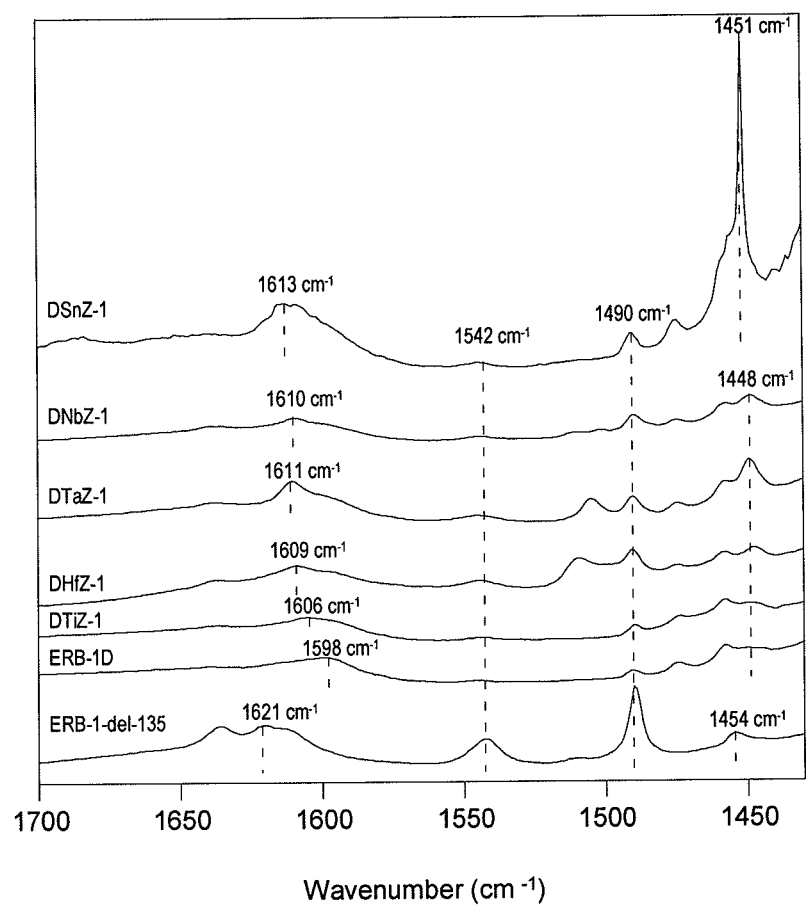
FIG. 18 shows FT-IR characterization of pyridine adsorption on DSnZ-1, DNbZ-1, DTaZ-1, DHfZ-1, DTiZ-1, ERB-1D, and ERB-1-del-135.
Figure 24:
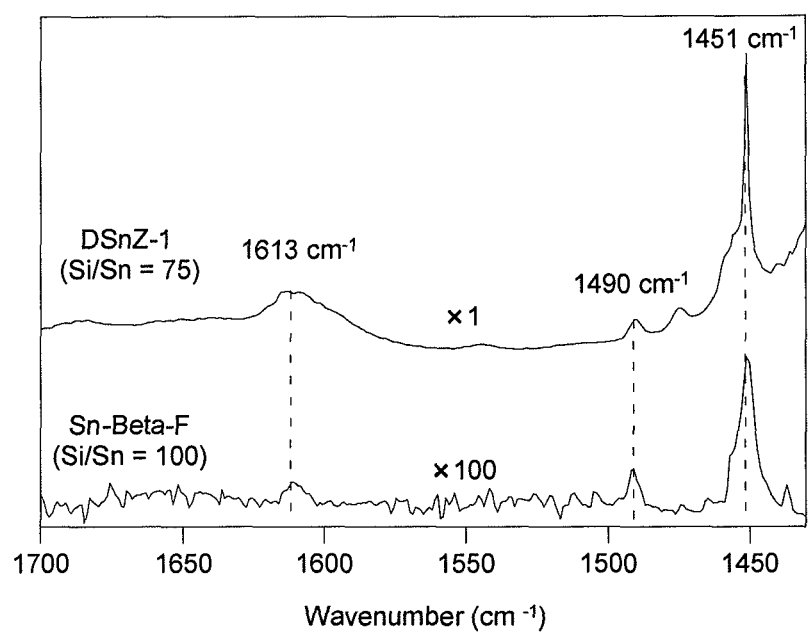
FIG. 24 shows FT-IR characterization of pyridine adsorption on DSNZ-1 and Sn-beta.

Pyridine adsorption was used as a tool to characterize the Brønsted and Lewis acidity of heteroatom-containing delaminated zeolites, as shown in FIG. 18. ERB-1-del-135 presents a large amount of Brønsted acidity (1542 cm$^{-1}$), whereas the other materials do not show noticeable Brønsted acidity. All materials showed a certain level of Lewis acidity. DSnZ-1 shows relatively stronger Lewis acidity (indicated by 1451 and 1613 cm$^{-1}$) than other materials. DNbZ-1, DTaZ-1, and DHfZ-1 show very similar Lewis acidity. FIG. 24 shows the comparison of DSnZ-1 versus Sn-beta for pyridine adsorption characterized by FT-IR spectroscopy. It is interesting to see that DSnZ-1 shows much higher (~100-fold) accessibility to pyridine than Sn-beta, which is probably due to the stronger hydrophobicity in Sn-beta.

Mechanisms of Delamination Via Isomorphous Substitution of al for B T-Positions

Figure 8:
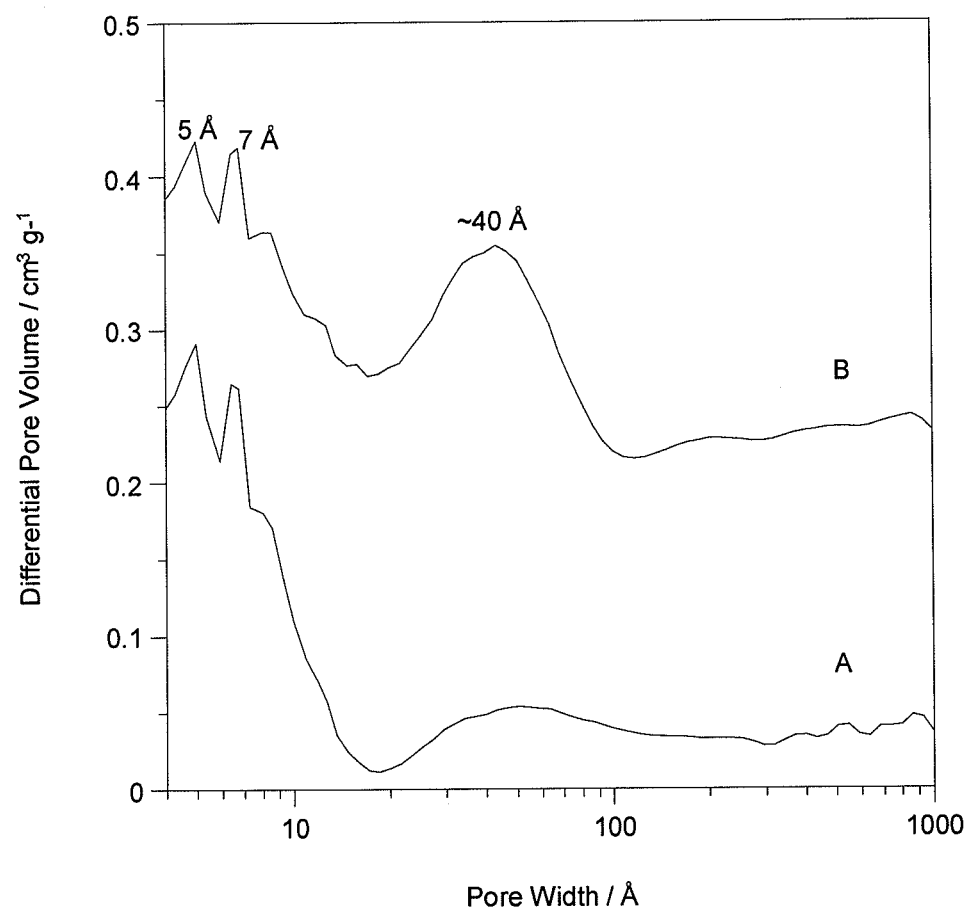
FIG. 8 shows $N_2$ NLDFT differential pore volume plots over pore width distributions up to 1000 Å for (A) ERB-1C and (B) ERB-1-del-135.

Several comparative studies were conducted to investigate the mechanisms of delamination of layered zeolite precursors via isomorphous substitution. First, two roles of $Al(NO_3)_3$ solution for delamination were considered, (1) the $Al(NO_3)_3$ solution contains $Al(H_2O)_6{}^+$ which was proved to be able to replace framework B by Al and create lattice distortion; and, (2) the $Al(NO_3)_3$ solution is acidic, pH≈2, which can partially leach out piperidine (TGA analysis, FIG. 8) and framework B. These two roles might play synergistic effects for delamination. To explore whether the foreign cation, $Al(H_2O)_6{}^{3+}$, is necessary for delamination, we treated ERB-1P in acids only, i.e., diluted HNO$_3$ solution (pH=2) at 135° C. or r.t., and 50 wt % acetic acid (pH≈1.5) at 135° C., and none of these $Al(H_2O)_6{}^{3+}$-free conditions show any success in delamination (as shown in Table 2 below). Instead, there was even slight decrease in micropore volume and external surface area, probably due to partial collapse of zeolite structure caused by the loss of framework B. Therefore, $Al(H_2O)_6{}^+$ and $H_3O^+$ probably both play important roles during the delamination.

TABLE 2

Comparative studies of delamination [a] of various layered zeolite precursors.

| samples | SDA | reagent | Si/Al ratio | Si/B ratio | 3D zeolite $V_{micro}$ (cm³/g) | 3D zeolite $S_{ext}$ [b] (m²/g) | After delamination $V_{micro}$ (cm³/g) | After delamination $S_{ext}$ [b] (m²/g) |
|---|---|---|---|---|---|---|---|---|
| ERB-1P | 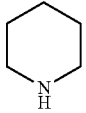 | $HNO_3$ [c]<br>$HNO_3$ (r.t.) [d]<br>HAc [e] | n/a | 11 | 0.12 | 53 | 0.06<br>0.15<br>0.10 | 13<br>25<br>20 |
| MCM-22P |  | $Al(NO_3)_3$ | 27 | n/a | 0.14 | 56 | 0.12 | 55 |
| Na-kanemite | n/a | $Al(NO_3)_3$ | | | | | | |
| B-SSZ-25 |  | $Al(NO_3)_3$ | n/a | 35 | 0.13 | 30 | 0.11 | 23 |
| B-SSZ-70 | 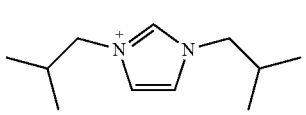 | $Al(NO_3)_3$ | n/a | 30 | 0.18 | 54 | 0.18 | 55 |

[a] The delamination was conducted on 200 mg of each zeolite precursor in 0.4N Al(NO₃)₃ solution at 135° C. for 1 d. The resulting materials were calcined in air at 550° C. for 5 h to remove SDAs.
[b] External surface area determined by t-plot method.
[c] 200 mg of ERB-1P was treated with HNO₃ solution, pH = 2, at 135° C. for 1 d, and then calcined in air at 550° C. for 5 h.
[d] Same as [c], except that the treatment was conducted at room temperature for 1 d.
[e] 200 mg of ERB-1P was treated with 50 wt % HAc solution at 135° C. for 1 d, and then calcined in air at 550° C. for 5 h.

Next, the delamination with $Al(NO_3)_3$ solution was attempted on several other layered zeolite/silicate precursors, including MCM-22P,[49] Na-kanemite,[50] B-SSZ-25,[51] B-SSZ-70, and B-magadiite. There are two factors to consider when choosing reference materials, (1) whether B is present in the framework of zeolite precursors; (2) whether the SDA is a small neutral amine or a rigid and large quaternary amine. MCM-22P does not have any B in its framework, so they can be used to study whether B is necessary for delamination. MCM-22P was prepared with neutral amines as SDAs, while B-MWW, and B-SSZ-70 were prepared with quaternary amines as SDAs, therefore, the comparison between these two groups can testify whether the delamination is dependent on the type of SDAs. Finally, Na-kanemite can be another reference since it has neither B nor SDA. The results of the efficiency of delamination on these mentioned layered zeolite precursors are listed in Table 2.

The SDA (hexamethyleneimide, HMI) for MCM-22P synthesis is structurally similar to piperidine, and its leaching in $Al(NO_3)_3$ solution is also in a similar case as ERB-1P (FIG. 7). However, the attempt to delaminate MCM-22P with $Al(NO_3)_3$ solution was unsuccessful, as no increase in external surface area was achieved (as shown in Table 2), suggesting that partial loss of SDA would not lead to delamination. The SDAs for B-SSZ-25 and B-SSZ-70 syntheses were very rigid and large quaternary amines. It was found that there is no leaching of SDAs after delamination as determined TGA analysis (FIG. 8), suggesting that these SDAs might have poor mobility because of steric effect inside the zeolite pores and channels. There was no increase in external surface area for B-SSZ-25 and B-SSZ-70 after treating with $Al(NO_3)_3$ solution (as shown in Table 2), thus it is believed that a relatively small and non-rigid SDA molecule is required for delamination.

Friedel Craft Acylation Over 3D and Delaminated Zeolites

The acylation of 2-methoxynaphthalene (2MN) with acetic anhydride ($Ac_2O$) in liquid phase was considered as an ideal model reaction to test the catalytic properties of the 3D and delaminated ERB-1 catalysts. The acylation of 2MN by $AlCl_3$ was a step in the first large-scale synthesis of naproxen, a drug commonly used for the relief of pain, fever, and inflammation. Because of current environmental restrictions, replacement of conventional homogeneous acid catalysts with solid acid catalysts, such as zeolites, has great industrial importance. The acylation of 2MN has been investigated over many molecular sieve catalysts, e.g., MCM-41, HY, ZSM-12 and *BEA. Two products are usually obtained, 1acetyl-2-methoxynapthalene (1,2-AMN) and 2-acetyl-6-methoxynaphthalene (2,6-AMN), with the kinetically favored but undesirable 1,2-AMN product generally predominating (>95%). The results from all previous studies show that almost all of the solid acid catalysts do not show any selectivity for desirable 2,6-AMN, except *BEA, which has a 3-dimentional 12MR channel system and can achieve ~50% selectivity for 2,6-AMN because of its shape selectivity within 12MR channels.

The results of the acylation of 2MN with acetic anhydride over the delaminated ERB-1 catalysts and 3D zeolites for comparison are listed in Table 3 below. First, it should be noted that the ratios of conversions of A₂O and 2MN over all zeolites are close to 1.7~2.2. The higher conversion of A₂O than 2MN is probably due to side reaction between the Brønsted acid sites, Si(OH)Al, with A₂O to form Si(O⁻CH₃—C⁺=O)Al and CH₃COOH. The conversions of 2MN for the delaminated ERB-1 catalysts follows the order as, ERB-1-del135>ERB-1-del-150>ERB-1-del-100>ERB-1-del-175, which is consistent with their order of external surface areas and uptakes of acridine. Therefore, higher degree of delamination does lead to higher activity for Friedel Craft acylation. The selectivity for 1,2AMN over the delaminated ERB-1 catalysts are all above 95%, which suggests that their acid sites essentially behave as true surface acid sites without any shape selectivity for acylation of 2MN. As shown in Table 3, only H-beta has shape selectivity to 2,6-AMN.

Interestingly, the activities for acylation of 2MN over the delaminated ERB-1 catalysts are not superior to their 3D counterpart, ERB-1C-Al, and other 3D zeolites listed in Table 3, even though they have lower Si/Al ratios and much more accessible acid sites. It is believed in the present case that the delaminated zeolites have significantly higher densities of surface silanol groups (confirmed by 3747 cm⁻¹ peak in FT-IR) and Si(OH)Al sites (confirmed by 3620 cm⁻¹ peak in FT-IR), and they both increase the hydrophilicity of the surface which inhibits the adsorption of 2MN to zeolite framework. Dealumination is considered a simple and effective way to increase hydrophobicity of zeolites and improve the activity for Friedel Craft acylation. By choosing ERB-1-del-135 for dealumination, it was found that an increase of Si/Al from 15 to 30 has boosted the conversion of 2MN from 20.4% to 41.2%, with no change in product selectivity.

Baeyer-Villiger Oxidation

Figure 19:
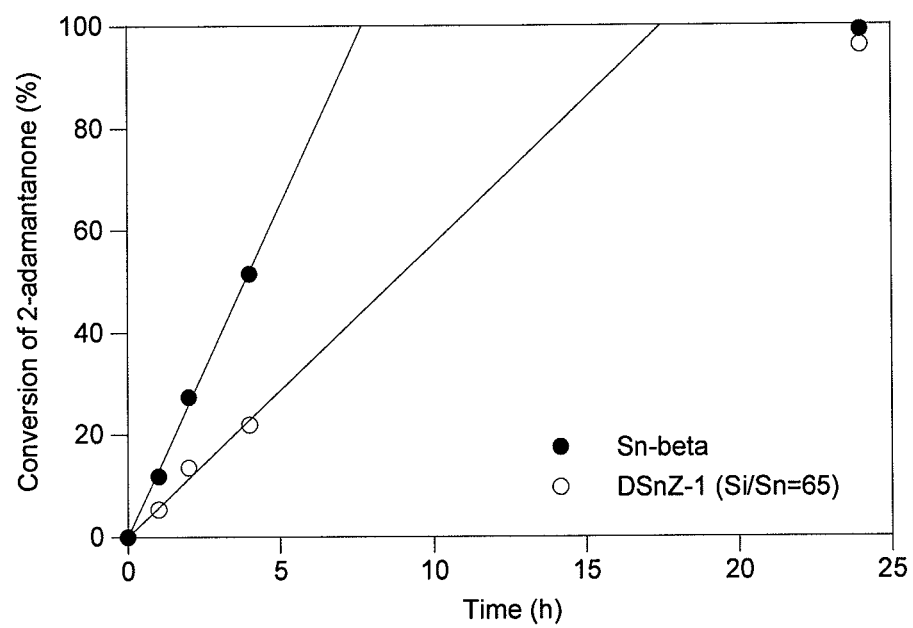
FIG. 19 graphically shows results of Baeyer-Villiger oxidation of 2-adamantanone by $H_2O_2$ over DSnZ-1 and Sn-beta.
Figure 20:
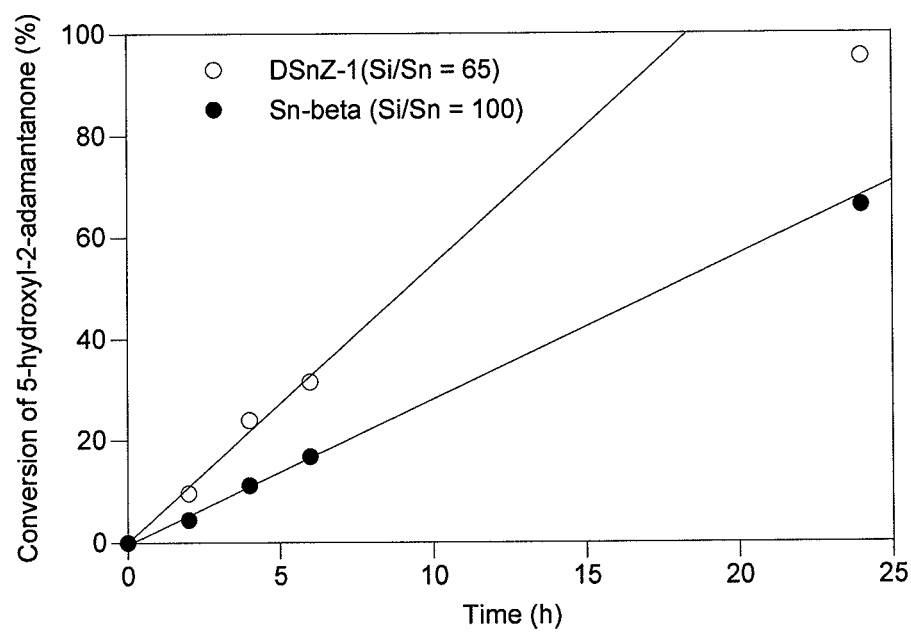
FIG. 20 graphically shows results of Baeyer-Villiger oxidation of 5-hydroxyl-2-adamantanone by $H_2O_2$ over DSnZ-1 and Sn-beta.
Figure 21:
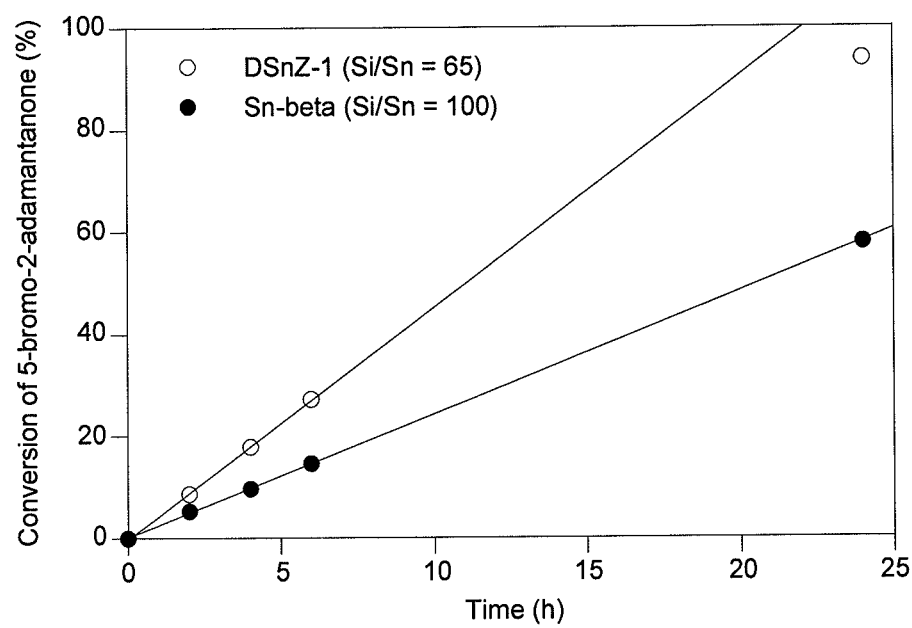
FIG. 21 graphically shows results of Baeyer-Villiger oxidation of 5-bromo-2-adamantanone by $H_2O_2$ over DSnZ-1 and Sn-beta.

Baeyer-Villiger oxidation was conducted on both DSnZ-1 and Sn-Beta, which is a bench-mark commercial catalyst for Baeyer-Villiger oxidation. When 2-adamantanone is used as the ketone reactant, the initial rate for Sn-beta is 2.2-fold higher (per Sn site) than the as-made DSnZ-1, as shown in FIG. 19. However, when more bulky 5-hydroxyl-2-adamantanone (FIG. 20) or 5-bromo-2-adamantanone (FIG. 21) is used as the ketone reactant, the initial rates (per Sn site) for as-made DSnZ-1 is 1.9-fold higher than Sn-Beta. The catalytic activity for DSnZ-1 is not limited by steric effects because all of the active Sn sites are located within 12-MR pockets on the external surface. On the other hand, the 12-MR in Sn-Beta is too small to fit in 5-hydroxyl-2-adamantanone and 5-bromo-2-adamantanone molecules. Therefore, only the Sn sites on the external surface of Sn-Beta are able to catalyze the reaction, which caused the observed drop of catalytic activity by almost 4-fold relative to the utility of smaller ketones.

Figure 22:
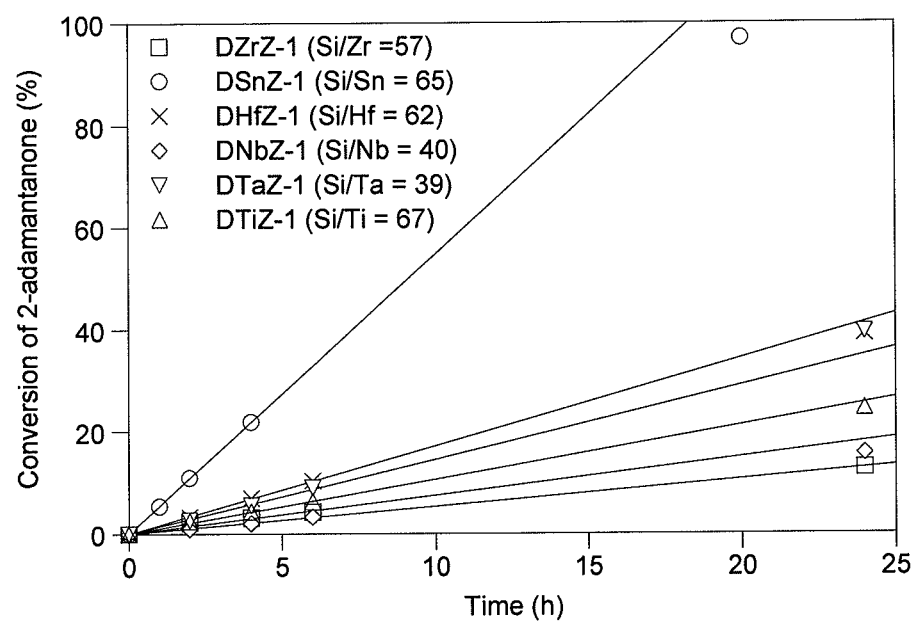
FIG. 22 graphically shows results of Baeyer-Villiger oxidation of 2-adamantanone by $H_2O_2$ over DSnZ-1, DZrZ-1, DHfZ-1, DNbZ-1, DTaZ-1, and DTiZ-1.

FIG. 22 shows the comparison of the catalytic activity of Baeyer-Villiger oxidation for DSnZ-1, DHfZ-1, DTaZ-1, DTiZ-1, DZrZ-1, and DNbZ-1. The activity for oxidizing 2-adamantanone by H₂O₂ follows the order of Sn>Hf>Ta>Ti>Zr>Nb.

Olefin Epoxidation

Figure 23:
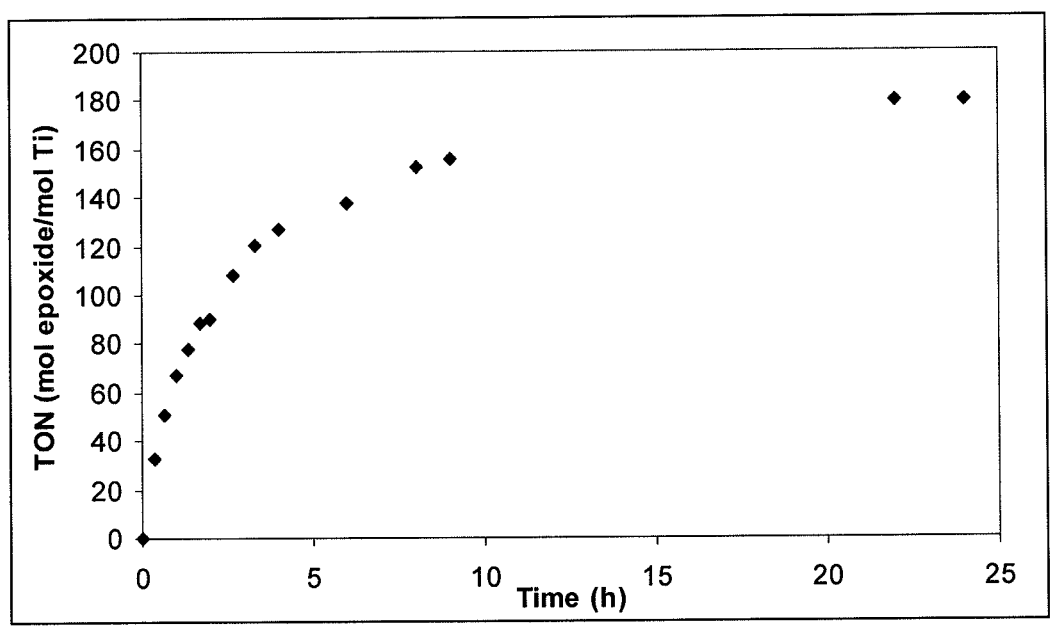
FIG. 23 graphically shows result of Epoxidation of 1-octene by TBHP over DTiZ-1.

Olefin epoxidation was tested on DTiZ-1.1-octene is used as the reductant, and TBHP is the oxidant. DTiZ-1 is catalytically active for olefin epoxidation and the TON at 2 hours is around 50, as shown in FIG. 23. Cyclohexene is used as a more bulky reactant for epoxidation over both DTiZ-1 and TS-1, which is the benchmark commercial titanosilicate catalysts. Due to steric effects, TS-1 shows almost no conversion of cyclohexene, whereas DTiZ-1 shows TON of 129 at 2 hours. This result speaks to the external-site nature of Ti sites in DTiZ-1, which is impossible to accomplish at such a high site density with TS-1.

Meerwein-Ponndorf-Verley (MPV) Reduction

Given the olefin epoxidation catalytic activity using solid Lewis-acid catalysts described above and discussed in Example [Olefin Epoxidation] above, catalytic activity for MPV reduction is also expected for all heteroatom-containing delaminated zeolites described in this invention. This is based on the fact that many solid Lewis-acid catalysts are active for both reactions (Nandi P.; Tang W. J.; Okrut A.; Kong X. Q.; Hwang S. J.; Neurock M.; Katz A. PNAS, 110, 2484-2489). Thus it is expected that materials (DSnZ-1, DTiZ-1, DZrZ-1, DHfZ-1, DNbZ-1, and DTaZ-1) are also active for MPV reduction, since all of these materials show activity either for Baeyer-Villiger oxidation or olefin epoxidation).

TABLE 3

Acylation of 2MN catalyzed by ERB-1 related zeolites. (Reaction condition: 100 mg of catalyst, 120° C., Ac₂O:2MN, 1:1 and 1.1 mmol, 10 mL of dichloroethane)

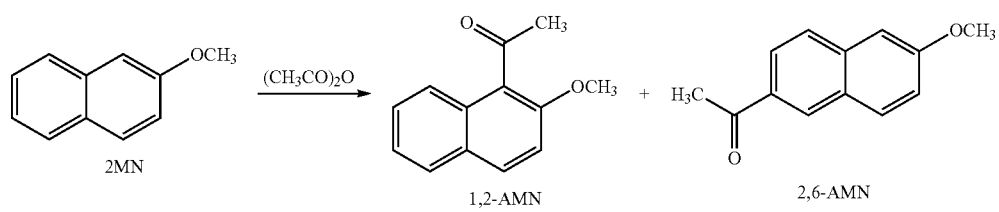

| sample | Conversion (%) | | | Yield (%) | | Selectivity (%) | |
|---|---|---|---|---|---|---|---|
| | 2MN | Ac₂O | Ac₂O/2MN ᵉ | 1,2-AMN | 2,6-AMN | 1,2-AMN | 2,6-AMN |
| ERB-1-del-100 | 14.5 | 31.3 | 2.2 | 13.9 | 0.6 | 95.7 | 4.3 |
| ERB-1-del-135 | 20.4 | 36.6 | 1.8 | 19.4 | 0.9 | 95.7 | 4.3 |
| ERB-1-del-150 | 16.1 | 32.3 | 2.0 | 15.2 | 0.8 | 95.2 | 4.8 |
| ERB-1-del-175 | 13.5 | 26.0 | 1.9 | 8.6 | 0.4 | 95.5 | 4.5 |
| ERB-1-del-135' ᵃ | 41.2 | 77.6 | 1.9 | 38.2 | 1.8 | 95.4 | 4.6 |
| ERB-1C-Al | 18.0 | 29.8 | 1.7 | 17.6 | 0.8 | 95.6 | 4.4 |
| H-beta ᵇ | 38.7 | 70.3 | 1.8 | 18.4 | 18.3 | 50.1 | 49.9 |

TABLE 3-continued

Acylation of 2MN catalyzed by ERB-1 related zeolites. (Reaction condition: 100 mg of catalyst, 120° C., Ac$_2$O:2MN, 1:1 and 1.1 mmol, 10 mL of dichloroethane)

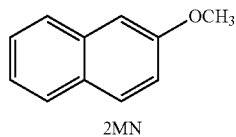

| | Conversion (%) | | | Yield (%) | | Selectivity (%) | |
|---|---|---|---|---|---|---|---|
| sample | 2MN | Ac$_2$O | Ac$_2$O/2MN [e] | 1,2-AMN | 2,6-AMN | 1,2-AMN | 2,6-AMN |
| H-MCM-22 [c] | 25.4 | 48.4 | 1.9 | 22.6 | 1.2 | 94.8 | 5.2 |
| H-SSZ-70 [d] | 29.9 | 50.0 | 1.7 | 28.3 | 1.8 | 93.9 | 6.1 |

[a] Prepared from dealumination of ERB-1-del-135. 200 mg sample was refluxed in 2N HNO$_3$ for 12 h. Si/Al = 30;
[b] Si/Al = 27;
[c] Si/Al = 40;
[d] Prepared from B-SSZ-70 via Al reinsertion, Si/Al = ?;
[e] The ratios of conversions of A$_2$O and 2MN.

Organosulfur Oxidation Including Sulfoxidation

Given the olefin epoxidation catalytic activity using solid Lewis-acid catalysts described above when using H$_2$O$_2$ as oxidant, it is expected that all heteroatom-containing delaminated zeolites described in this invention will also be active for organosulfur compound oxidation, and specifically, as a subset of this, for sulfoxidation. Sulfoxidation reactions include oxidizing a sulfide to a sulfone, and oxidizing a sulfone to a sulfoxide. Several zeolites that are substituted with Lewis-acid heteroatoms within the framework are active for sulfoxidation (see examples with Ti and V in Catalysis Letters 1993, 22, 239-249). Within this context, sulfoxidation refers to the oxidation of sulfur in an organosulfur compound. Such organosulfur oxidations are useful industrially for facilitating organosulfur compound removal from liquid mixtures and specifically from fuels, where their amounts are tightly controlled via environmental regulations. Thus, there is an ongoing need for organosulfur oxidation, and all heteroatom-containing delaminated zeolites described in this invention are expected to be able to meet this need based on their observed activity for Bayer-Villiger oxidation using H$_2$O$_2$ as well as olefin epoxidation.

The foregoing experimental runs demonstrated that the present invention provides a simple method to delaminate layered borosilicate zeolite precursors through isomorphous substitution of B by Al. Characterization by PXRD, NMR, N$_2$ physisorption, TEM, FT-IR, and base titration confirms the decrease of micropore volume and increase of external surface area in the delaminated ERB-1 catalysts. The temperature plays an important role in controlling the efficiency of delamination. The delamination of ERB-1P at 135° C. was more efficient than at 100 or 175° C. This new delamination method might be suitable for various layered borosilicate zeolite precursors synthesized with small and neutral amine SDAs, but less efficient for the ones synthesized with rigid and large quaternary amine SDAs. Acylation of 2MN was used as a model reaction to test the activity and selectivity of the delaminated ERB-1 catalysts. Among the delaminated ERB-1 catalysts, the activity for the acylation of 2MN is proportional to their external surface area, but they all behave as surface acid sites without showing any shape selectivities. Dealumination of the delaminated ERB-1 catalysts further improves the activity for the acylation of 2MN significantly, suggesting that besides delamination, increasing hydrophobicity of the catalysts should also be emphasized.

TABLE 4

Results from nitrogen physisorption measurement of ERB-1-del-Zn materials.

| Sample | V$_{micro}$ (cm$_3$/g) | V$_{meso}$ (cm$_3$/g) | S$_{ext}$ (m$^2$/g) |
|---|---|---|---|
| ERB-1-C | 0.12 | 0.04 | 53 |
| As-made ERB-1-del | 0.02 | 0.11 | 122 |
| Calcined ERB-1-del | 0.17 | 0.10 | 131 |
| As-made Ti-ERB-1-del | 0.03 | 0.14 | 171 |

Figure 9:
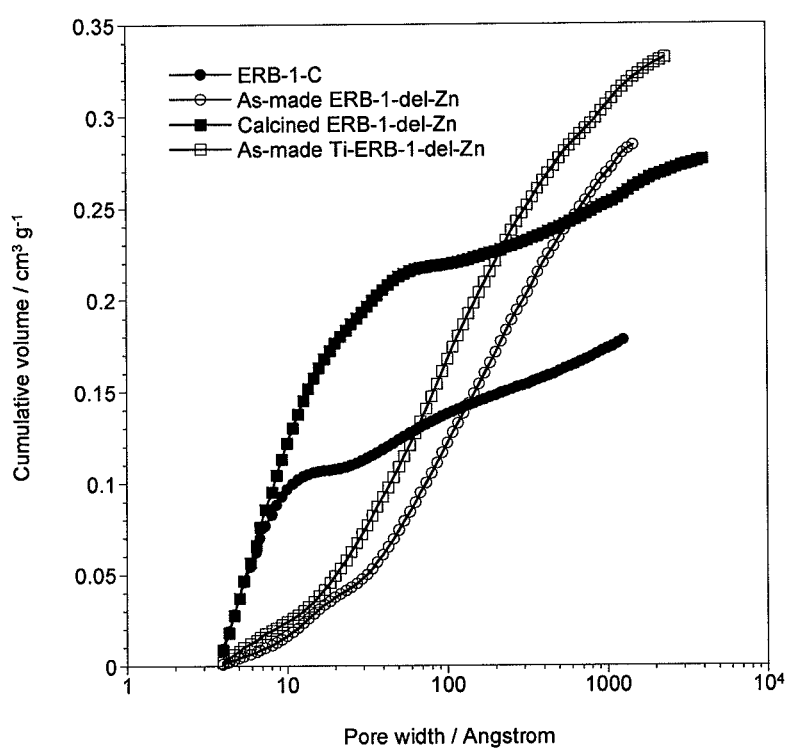
FIG. 9 shows N2 NLDFT cumulative pore volume plots for ERB-1C, as-made ERB-1-del-Zn, Calcined ERB-1-del-Zn, and as-made Ti-ERB-1-del-Zn.

Data in FIG. 9 and summarized in Table 4 demonstrate a significant increase in external surface area for as-made ERB-1-del-Zn, calcined ERB-1-del-Zn, and as-made TiERB-1-del-Zn, all relative to material ERB-1C. This external surface-area comparison across various calcined and as-made (uncalcined) materials is valid because a comparison of calcined ERB-1-del-Zn and as-made ERB-1-del-Zn demonstrates that calcination does not change external surface area appreciably (i.e. change is less than 10%). Thus, these data are consistent with materials as-made ERB-1-del-Zn, calcined ERB-1-del-Zn, and as-made TiERB-1-del-Zn all being delaminated relative to material ERB-1C, since their external surface areas are significantly larger.

Overall, this invention can be applied to the production of delaminated aluminosilicate zeolite materials which have disordered stacking of thin zeolitic sheets (~2.5 nm) with high and structurally well defined, external surface, as well as high density of accessible acid sites.

The delaminated MWW aluminosilicate zeolite materials prepared by this new delamination method can be applied as solid acid catalysts in acid-catalyzed reactions, such as isomerization, alkylation, acylation, cracking, hydrolysis, etc.

The delaminated MWW aluminosilicate zeolite materials prepared by this new delamination method can be used for ion exchange in various industries, such as water treatment, redioactive pollutant removal, aquaculture, agriculture, horticulture, etc.

The delaminated MWW aluminosilicate zeolite materials prepared by this new delamination method can be used for water adsorption and desorption.

The delaminated MWW aluminosilicate zeolite materials prepared by this new delamination method can be used as zeolitic membrane materials for gas separation.

All patents and publications referenced herein are hereby incorporated by reference, in their entirety, to the extent not inconsistent with the present disclosure. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A process for delaminating a borosilicate layered zeolite precursor comprising contacting said zeolite precursor in a solution containing a metal salt wherein the borosilicate layered zeolite precursor is ERB-1.

2. The process of claim 1 wherein the metal salt comprises an Al, Zn or Mn cation.

3. The process of claim 1 wherein the metal salt comprises a Ga cation.

4. The process of claim 1, wherein the delamination is conducted at a temperature in the range of from 100-170° C.

5. The process of claim 4, wherein the temperature is in the range of from 125-145° C.

6. The process of claim 4, wherein the temperature is about 135° C.

7. A delaminated zeolite resulting from the process of claim 1.

8. The delaminated zeolite of claim 7 containing metal atoms from the metal salt.

9. The delaminated zeolite of claim 7 containing aluminum atoms.

10. A dealuminated material obtained by removing at least a portion of the aluminum atoms from the delaminated zeolite of claim 9.

11. A demetallated material obtained by removing at least a portion of the metal atoms from the delaminated zeolite of claim 8.

12. A Lewis-acid catalysis reaction process comprising contacting an organic feed with a catalyst comprising the zeolite of claim 11.

13. The catalytic reaction process of claim 12, wherein the reaction is an olefin epoxidation.

14. The catalytic reaction process of claim 12, wherein the reaction is an MIN reduction.

15. The catalytic reaction process of claim 12, wherein the reaction is an organosulfur oxidation.

16. A reaction process comprising contacting a hydrocarbon feed with a catalyst comprising the zeolite of claim 7, with the catalyst comprising a metal selected from the group consisting of Ti, Sn, V, La, Zr, Hf, Nb and Ta atoms.

17. A reaction process comprising contacting a hydrocarbon feed with a catalyst comprising the zeolite of claim 7 under acid catalysis conditions.

18. The reaction process of claim 17, wherein the reaction is run under conditions for isomerization, alkylation, acylation, cracking or hydrolysis.

19. A process for preparing a delaminated aluminosilicate zeolite comprising the step of exfoliating the borosilicate layered zeolite of claim 1 via isomorphous substitution of Al for B T-positions by refluxing the borosilicate zeolite in an aluminum salt aqueous solution.

20. The process of claim 19, wherein the aluminum salt solution is an aluminum nitrate solution.

* * * * *

UNITED STATES PATENT AND TRADEMARK OFFICE
CERTIFICATE OF CORRECTION

PATENT NO. : 9,795,951 B2  
APPLICATION NO. : 14/291489  
DATED : October 24, 2017  
INVENTOR(S) : Xiaoying Ouyang et al.

Page 1 of 1

It is certified that error appears in the above-identified patent and that said Letters Patent is hereby corrected as shown below:

In Claim 14, Line 18, please delete "MIN" and insert --MPV-- in place thereof.

Signed and Sealed this
Twenty-seventh Day of March, 2018

Andrei Iancu
*Director of the United States Patent and Trademark Office*